US011266652B2

(12) United States Patent
Symonds et al.

(10) Patent No.: US 11,266,652 B2
(45) Date of Patent: Mar. 8, 2022

(54) METHODS OF TREATING SUBJECTS HAVING DIABETES WITH CHRONIC KIDNEY DISEASE

(71) Applicant: Poxel SA, Lyons (FR)

(72) Inventors: Bill Symonds, Cary, NC (US); Steve Piscitelli, Hillsborough, NC (US); Karen Segal, New York, NY (US); Ruby Holder, New York, NY (US); Sophie Bozec, Antony (FR); Sebastien Bolze, Massieux (FR); Pascale Fouqueray, Lyons (FR); Christophe Arbet-Engels, Wellesley, MA (US); Julie Dubourg, Lyons (FR); Paul Strumph, Moneta, VA (US); Brandon Dale Swift, Apex, NC (US); Margaret Smith Fletcher, San Clemente, CA (US)

(73) Assignee: POXEL SA, Lyons (FR)

( * ) Notice: Subject to any disclaimer, the term of this patent is extended or adjusted under 35 U.S.C. 154(b) by 0 days.

(21) Appl. No.: 16/813,436

(22) Filed: Mar. 9, 2020

(65) Prior Publication Data
US 2020/0215072 A1    Jul. 9, 2020

Related U.S. Application Data

(63) Continuation of application No. PCT/US2019/035789, filed on Jun. 6, 2019.

(60) Provisional application No. 62/681,391, filed on Jun. 6, 2018.

(51) Int. Cl.
A61K 31/53    (2006.01)
A61P 3/10     (2006.01)
A61P 13/12    (2006.01)

(52) U.S. Cl.
CPC ............ *A61K 31/53* (2013.01); *A61P 3/10* (2018.01); *A61P 13/12* (2018.01)

(58) Field of Classification Search
CPC ............ A61K 31/53; A61P 3/10; A61P 13/12
See application file for complete search history.

(56) References Cited

U.S. PATENT DOCUMENTS

| | | | |
|---|---|---|---|
| 3,287,366 A | 11/1966 | Newman et al. | |
| 7,034,021 B2 | 4/2006 | Moinet et al. | |
| 7,452,883 B2 | 11/2008 | Moinet et al. | |
| 7,501,511 B2 | 3/2009 | Moinet et al. | |
| 7,767,676 B2 | 8/2010 | Moinet et al. | |
| 8,217,040 B2 | 7/2012 | Moinet et al. | |
| 8,227,465 B2 | 7/2012 | Moinet et al. | |
| 8,461,331 B2 | 6/2013 | Helmreich et al. | |
| 8,592,370 B2 | 11/2013 | Mesangeau et al. | |
| 8,742,102 B2 | 6/2014 | Helmreich et al. | |
| 8,742,103 B2 | 6/2014 | Cravo et al. | |
| 8,791,115 B2 | 7/2014 | Moinet et al. | |
| 8,846,911 B2 | 9/2014 | Maillard et al. | |
| 8,937,066 B2 | 1/2015 | Mesangeau et al. | |
| 8,980,828 B2 | 3/2015 | Mesangeau et al. | |
| 9,035,048 B2 | 5/2015 | Cravo et al. | |
| 9,271,984 B2 | 3/2016 | Fouqueray et al. | |
| 2006/0223803 A1 | 10/2006 | Moinet et al. | |
| 2010/0256368 A1 | 10/2010 | List et al. | |
| 2013/0177604 A1* | 7/2013 | Baron ............... | C07D 307/52 424/400 |
| 2017/0304262 A1 | 10/2017 | Nalk et al. | |

FOREIGN PATENT DOCUMENTS

| | | |
|---|---|---|
| JP | 4864088 A | 9/1973 |
| JP | 5414986 | 2/1979 |
| JP | 6141915 B2 | 9/1986 |
| TW | 200504037 A | 2/2005 |
| WO | WO 99/31088 A1 | 6/1999 |
| WO | WO 01/55122 A1 | 8/2001 |
| WO | WO 2004/089917 A2 | 10/2004 |
| WO | WO 2005/070905 A1 | 8/2005 |
| WO | WO 2007/079915 A2 | 7/2007 |
| WO | WO 2009/062483 A2 | 5/2009 |
| WO | WO 2010/066901 A2 | 6/2010 |
| WO | WO 2011/154497 A1 | 12/2011 |
| WO | WO 2014/161919 A1 | 10/2014 |
| WO | WO 2019/069230 A1 | 4/2019 |
| WO | WO 2019/236844 A1 | 12/2019 |

OTHER PUBLICATIONS

Arnouts; P. et al., "Glucose-lowering drugs in patients with chronic kidney disease: a narrative review on pharmacokinetic properties," Nephrol Dial Transplant 29:1284-1300, Oxford University Press, England (2013).
Bezold M.A., "Vergleich der Auswirkung einer oralen therapie mit metformin und EMD 387008 auf renale Schaden im Tiermodell der diabetogenen ZDF-Ratte/comparing the effects of oral therapy with metformin and EMD387008 to renal damage in the animal model of the diabetic ZDF rat," Doctoral Thesis p. 108 (2010).
Dubourg; J. et al., "Imeglimin monotherapy in Japanese patients with type 2 diabetes: results from a randomized, 24-week, double-blind, placebo-controlled, phase IIb trial," EASD 2017 Session PS066 Novel Approaches to glucose-lowering, Poster, Poxel (2017).
Dubourg; J. et al., "843—Imeglimin monotherapy in Japanese patients with type 2 diabetes: results from a randomised, 24-week, double-blind, placebo controlled, phase IIb trial, Session F PS066 novel Approaches to glucose-lowering," (2017), Abstract.
Marin-Penalver; J.J. et al., "Update on the treatment of type 2 diabetes mellitus," World J. Diabetes 7(17):354-95, Baishideng Publishing Group, United States (2016).
Palsson; R. et al. "Cardiovascular complications of diabetic kidney disease," Adv. Chronic. Kidney Dis. 21(3):273-80, Elsevier, Netherlands (2014).

(Continued)

Primary Examiner — Sahar Javanmard
(74) Attorney, Agent, or Firm — Goodwin Procter LLP

(57) ABSTRACT

The present disclosure is directed to a method of treating prediabetes or type 1 or type 2 diabetes mellitus comprising administering to a subject in need thereof an effective amount of imeglimin, wherein the subject has chronic kidney disease.

20 Claims, 13 Drawing Sheets

(56) References Cited

OTHER PUBLICATIONS

Pirags; V. et al., "Imeglimin, a novel glimin oral antidiabetic, exhibits a good efficacy and safety profile in type 2 diabetic patients," Diabetes, Obesity and Metabolism 14(9):852-8 (2012).
Pirags; V. et al., "Imeglimin, a novel glimin oral anti-diabetic, exhibits good glycemic control in Type 2 diabetic patients," Poster Presentation, Poxel (2010).
Poxel Corporate Presentation, Imeglimin and PXL770, Jan. 2017.
Press Release, "Poxel Announces Additional Positive Results for Imeglimin Phase 2b Study in Japan for the Treatment of Type 2 Diabetes," Poxel, Jun. 6, 2017.
Tuttle; K.R. et al., "Diabetic Kidney Disease: A Report From an ADA Consensus Conference," Diabetes Care 37(10): 2864-2883, American Diabetes Association (2014).
Vuylsteke; V. et al., "Imeglimin: A potential new mutli-target drug for type 2 diabetes," Drugs in R and D 15(3): 227-32 (2015).
International Search Report and Written Opinion for International Application No. PCT/US2019/035789, European Patent Office, Netherlands, dated Oct. 10, 2019, 9 pages.
Baumann, B. et al., "Anti-inflammatory therapy in type 1 diabetes," Abstract, Curr. Diab. Rep., 12(5):499-509 (2012).
Declaration Under Rule 132 by Dr. Daniel Cravo dated Mar. 5, 2014, from U.S. Appl. No. 13/703,138.
Declaration Under Rule 132, executed by Dr. E. Larger on May 22, 2015, from U.S. Appl. No. 13/703,147.
Declaration Under Rule 132, executed by Dr. S. Hallakou-Bozec on May 21, 2015, from U.S. Appl. No. 13/703,147.
Donath, M. et al., "Mechanisms of β-Cell Death in Type 2 Diabetes," Diabetes, 54(2):S108-S113 (2005).
English language Summary of Office Action dated Jun. 19, 2013, issued in Taiwanese Patent Application No. 100120015 including English language summary of TW200504037 A and WO2007/079915A2, from U.S. Appl. No. 13/703,138.
Fonseca, V.A., "Defining and Characterizing the Progression of Type 2 Diabetes," Diabetes Care, 32(2):S151-S156 (2009).
"International Nonproprietary Names for Pharmaceutical Substances (INN)," Who Drug Information, 1-56 (2007).
International Search Report and Written Opinion for International Application No. PCT/EP2011/059589, dated Sep. 20, 2011, 8 pages.
International Search Report and Written Opinion for International Application No. PCT/EP2011/059590, dated Sep. 21, 2011, 8 pages.
Knowler, W., et al, "Reduction in the Incidence of Type 2 Diabetes with Lifestyle Intervention or Metformin," The New England Journal of Medicine, 346(6):393-403 (2002).
Krischer, J., et al., "Screening Strategies for the Identification of Multiple Antibody-Positive Relatives of Individuals with Type 1 Diabetes," The Journal of Clinical Endocrinology & Metabolism, 881(1):103-108 (2003).
Marchetti, P., et al., "Pancreatic Islets from Type 2 Diabetic Patients Have Functional Defects and Increased Apoptosis That Are Ameliorated by Metformin," The Journal of Clinical Endocrinology & Metabolism, 89(11):5535-5541.
Modest, E.J., "Chemical and Biological Studies on 1,2-Dihydro-s-triazines. II. Three-Component Synthesis," The Journal of Organic Chemistry, 21(1):1-13 (1956).
Modest, E.J., "Chemical and Biological Studies on 1,2-Dihydro-s-triazines. III. Two Component Synthesis," The Journal of Organic Chemistry, 21(1):14-20 (1956).
Partial English translation of http:/mccli.ru/doc/a793705 cited Application No. EA201201623 (Fouqueray et al) by Eurasia Patent Office Organization in Office Action, dated Mar. 25, 2015, from U.S. Appl. No. 13/703,138.
Rembarz, V.G., et al., "Reaktinon mit Natriumdicyanimid," Journal fur praktische Chemie, 4(26):314-318 (1964) (English abstract attached).
Roth, B., et al., "Anthelmintic Agents. 1,2-Dihydro-s-Triazines," Journal of Medicinal Chemistry, American Chemical Society, 6(4):370-378 (1963).
Simmons, K., et al., "Type 1 diabetes: A predictable disease," World J. Diabetes, 6(3):380-390 (2015).
Sosenko, J., et al., "A Risk Score for Type 1 Diabetes Derived From Autoantibody-Positive Participants in the Diabetes Prevention Trial-Type 1," Diabetes Care, 31(3):528-533 (2008).
Stevens, M., et al., "Introduction of a triflate group into sterically hindered positions in 1-Aryl-4,6-diamino-1,3,5-triazines and their Dimroth Rearrangement Products," Journal of Heterocyclic Chemistry, 30(4):849-853 (1993).
Thornalley, P.J., "Use of aminoguanidine (Pimagedine) to prevent the formation of advanced glycation endproducts," Archives of Biochemistry and Biophysics, 419(1):31-40 (2003).
Tiikkainen, M., et al., "Effects of rosiglitazone and metformin on liver fat content, hepatic insulin resistance, insulin clearance, and gene expression in adipose tissue in patients with type 2 diabetes," Diabetes, 54:2169-2176 (2004).
Ziegler, A., et al., "Seroconversion to Multiple Islet Autoantibodies and Risk of Progression to Diabetes in Children," Journal of the American Medical Association, 309(23):2473-2479 (2013).
Sophie Hallakou-Bozec, et al., "Mechanism of action of Imeglimin A novel therapeutic agent for type 2 diabetes," Diabetes Obes. Metab. 2021;23:664-673.
Bristol-Myers Squibb., Glucophage package insert. U.S. Food and Drug Administration website <https://www.accessdata.fda.gov/drugsatfda_docs/label/2017/020357s037s039,021202s021s023lbl.pdf>. Revised Apr. 2017. Accessed May 10, 2021.

* cited by examiner

METHODS OF TREATING SUBJECTS HAVING DIABETES WITH CHRONIC KIDNEY DISEASE

FIELD OF THE INVENTION

The present invention relates to use of imeglimin for treating metabolic disorders, such as pre-diabetes, type 1 or type 2 diabetes mellitus, in patients with renal impairment or chronic kidney disease (CKD).

BACKGROUND

Metabolic disorders affect a patient's normal metabolic process and include pre-diabetes and type 1 or type 2 diabetes mellitus. Type 2 diabetes mellitus (T2DM) is a long-term metabolic disorder that is characterized by high blood sugar, insulin resistance, and relative lack of insulin. The prevalence of type 2 diabetes mellitus is increasing worldwide with approximately 451 million adults affected by diabetes in 2017; this number is anticipated to increase to 693 million adults in 2045. This global epidemic of diabetes imposes an enormous individual, societal and economic burden, particularly in the presence of polyvascular complications of diabetes. Pre-diabetes is the precursor stage before diabetes mellitus in which not all of the symptoms required to diagnose diabetes are present, and blood sugar is higher than normal but not high enough to be called diabetes. Pre-diabetes is associated with obesity (especially abdominal or visceral obesity), dyslipidemia with high triglycerides and/or low HDL cholesterol, and hypertension. It is thus a metabolic diathesis or syndrome, and it usually involves no symptoms and only high blood sugar as the sole sign. Type 1 diabetes, once known as juvenile diabetes or insulin-dependent diabetes, is a chronic condition in which the pancreas produces little or no insulin.

Chronic kidney disease (CKD) is a condition characterized by a gradual loss of kidney function over time. It is estimated that 30-50% of all people with diabetes are affected with chronic kidney disease: more than 40% of subjects with CKD also have T2DM. In addition, diabetes is the most frequent underlying cause of CKD and end-stage renal disease (ESRD), with T2DM present in more than 50% of incident ESRD cases. See Tuttle, et al. Diabetic kidney disease: a report from an ADA Consensus Conference, Diabetes Care. 2014; 37(10): 2864-2883.

Diabetic kidney disease is a chronic progressive disease with limited therapeutic options. Standard of care for this population includes therapy with an inhibitor of the renin angiotensin system (RAS) for renoprotection and diabetes care including management of hyperglycemia and cardiovascular disease risk factors as it is generally accepted that the coincidence of advanced CKD and T2DM presents a greatly accelerated cardiovascular (CV) risk. Palsson R, Patel U D, Cardiovascular complications of diabetic kidney disease, Adv. Chronic. Kidney Dis. 2014; 21(3):273-80. In fact, the excess mortality among patients with diabetes appears to be limited largely to the subgroup with kidney disease and explained by their high burden of cardiovascular disease.

It is clear that degree of glycemic abnormality predicts development of nephropathy and sustained, intensive glycemic control protects against the development of microvascular complications of diabetes. However, the long-term impact of intensive glycemic control on clinical outcomes in the population of patients with coincident T2DM and clinically significant CKD is less clear. Despite the availability of more than 15 classes of drugs for managing hyperglycemia in T2DM patients, many of these therapies are either not recommended or require significant dose reductions in the presence of concomitant moderate or severe CKD. Thus, there exists a need to develop better treatment options for diabetic patients with CKD, particularly moderate or severe CKD.

SUMMARY

Figure 1:
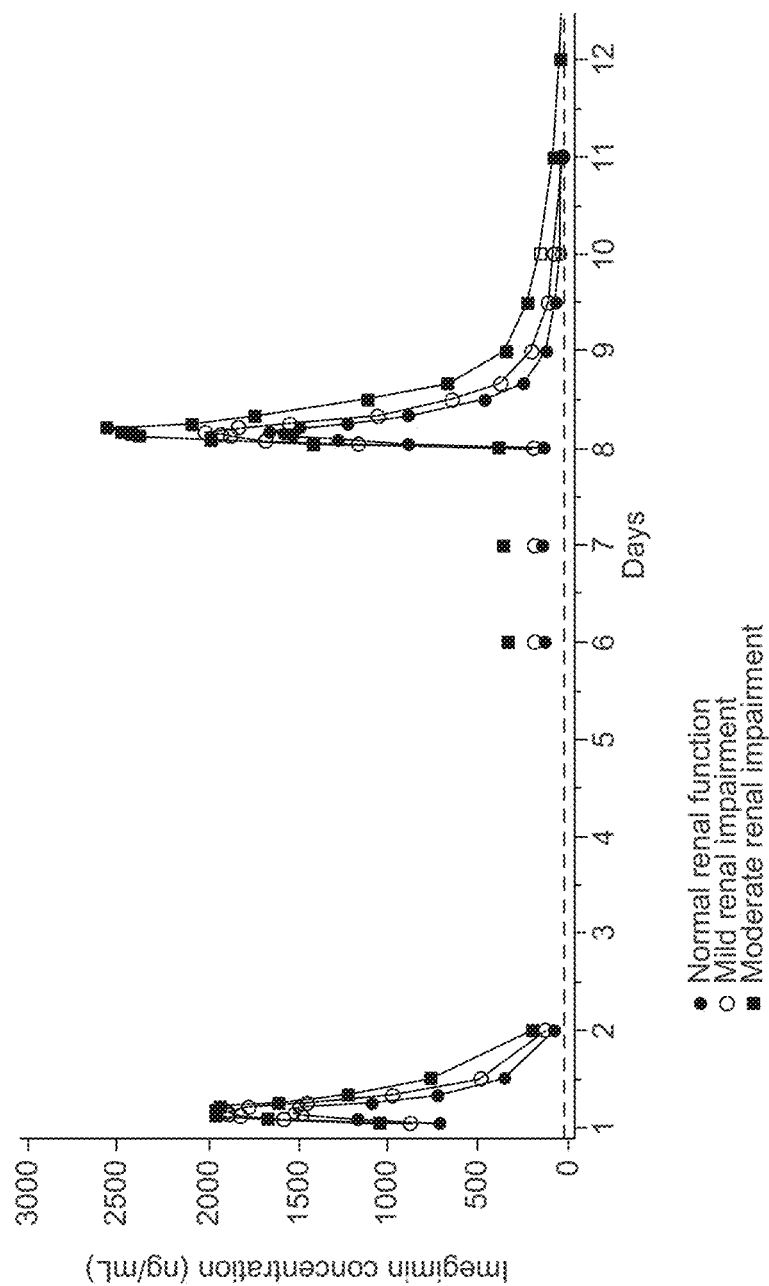
FIG. 1 depicts geometric mean plasma concentrations of imeglimin in subjects with differing degrees of renal impairment, following 1000 mg QD of imeglimin across all days in a Phase 1 study (Linear Scale).

The present disclosure provides a method of treating diabetes mellitus in subjects with chronic kidney disease, particularly moderate and severe CKD, the method comprising orally administering to a subject in need thereof an effective amount of imeglimin.

DETAILED DESCRIPTION

In order that the present disclosure can be more readily understood, certain terms are first defined. As used in this application, except as otherwise expressly provided herein, each of the following terms shall have the meaning set forth below. Additional definitions are set forth throughout the application.

In this specification and the appended claims, the singular forms "a," "an" and "the" include plural referents unless the context clearly dictates otherwise. The terms "a" (or "an"), as well as the terms "one or more," and "at least one" can be used interchangeably herein. In certain aspects, the term "a" or "an" means "single." In other aspects, the term "a" or "an" includes "two or more" or "multiple."

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C: A, B, or C; A or C; A or B; B or C; A and C; A and B; B and C; A (alone); B (alone); and C (alone).

Unless defined otherwise, all technical and scientific terms used herein have the same meaning as commonly understood by one of ordinary skill in the art to which this disclosure is related.

The term "about" as used in connection with a numerical value throughout the specification and the claims denotes an interval of accuracy, familiar and acceptable to a person skilled in the art. Such interval of accuracy is ±10%.

The term "treatment period" means the period of time during which the drug is administered to a subject and certain parameters of the subject are measured and compared to the baseline values. For example, the treatment period can be from about 2 weeks to about 2 years. In some embodiments, the treatment period can be about 2, about 4, about 6, about 8, about 10, about 12, about 14, about 16, about 18, about 20, about 24, about 52, about 76 or about 104 weeks. The efficacy of the drug can be assessed by measuring certain parameters and calculating the changes from baseline over the treatment period. The efficacy parameters include, but are not limited to, placebo-subtracted decrease in glycosylated hemoglobin (HbA1c) percentage and placebo-subtracted decrease in fasting plasma glucose (FPG).

The term "AUC" as used herein refers to the area under the curve of a plot of plasma concentration versus time following administration of a drug.

The present disclosure also describes a method of using imeglimin for treating subjects with pre-diabetes, or diabetes mellitus, and CKD stage 3B or stage 4. The present disclosure describes a method of using imeglimin for treating subjects with T2DM and CKD stage 3B or stage 4. The present disclosure also describes a method of using imeglimin for treating subjects with type 1 diabetes mellitus and CKD stage 3B or stage 4.

Management of hyperglycemia presents a particular challenge in subjects with diabetic kidney disease. Because of the loss of renal function in these subjects, many of the approved classes of anti-hyperglycemic therapies that are renally cleared require reduced doses or are not recommended. Thus, there are limited therapeutic options for diabetes management in subjects with kidney disease, and particularly moderate or severe CKD. Insulin and selected insulin secretagogues such as sulfonylurea medications are frequently used in this population; however, reduced clearance of insulin prolongs the duration of insulin action and thereby increases the risk of hypoglycemia events including severe hypoglycemia. Taking into consideration the substantial hypoglycemia risk of intensive glycemic control in CKD patients, recent clinical guidelines recommend a target HbA1c of 7.0% in the presence of moderate or severe CKD. See American Diabetes Association, Standards of Medical Care in Diabetes-2018.

Most approved anti-hyperglycemic therapies can be used in patients with an estimated glomerular filtration rate (eGFR) as low as 45 ml/min/1.73 m$^2$ (i.e., through CKD stage 3A). However, most therapies are dose-reduced or contraindicated in CKD stage 3B and 4 (eGFR 15-44 ml/min/1.73 m$^2$) affecting approximately 200,000 incident cases annually with nearly two million prevalent cases in the United States. For example, metformin is contraindicated in patients with an estimated glomerular filtration rate (eGFR) below 30 mL/minute/1.73 m$^2$, and not recommended for patients with an eGFR between 30-44 mL/minute/1.73 m$^2$. In addition, for many therapeutic agents that can be used in diabetic patients with CKD, they often lose efficacy as the patients' renal function declines. Accordingly, there is a limited set of safe and effective patient choices for glycemic control for the substantial number of patients with this degree of advanced diabetic kidney disease.

Imeglimin is disclosed as 5,6-dihydro-4-dimethylamine-2-imino-6-methyl-1,3,5-triazine and described in U.S. Pat. Nos. 7,034,021, 7,452,883, 7,767,676, 7,501,511, 8,227,465, 8,791,115, 8,217,040, 8,461,331, 8,846,911, 9,035,048, 8,742,102, 8,592,370, 8,980,828, 8,742,103, 9,271,984, and 8,937,066. According to World Health Organization (WHO) criteria, imeglimin can be referred to as (6R)—N$^2$,N$^2$,6-trimethyl-3,6-dihydro-1,3,5-triazine-2,4-diamine. Compound I is further known as imeglimin.

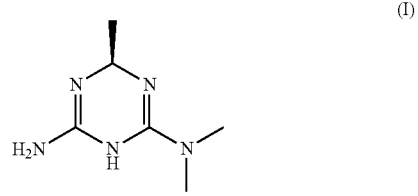

(I)

Imeglimin is the first in a new tetrahydrotriazine-containing class of oral antidiabetic agents, with a unique mechanism of action targeting mitochondria bioenergetics and function.

Imeglimin has been studied in subjects with T2DMs for up to 24 weeks as monotherapy and as add on to metformin and sitagliptin. In each study imeglimin was well-tolerated with a safety profile comparable to that of placebo and placebo-subtracted reductions in glycosylated hemoglobin (HbA1c) in the range of −0.42% to −0.72% for the dose of 1500 mg twice daily (BID).

The pharmacokinetics (PK) of imeglimin are characterized by less than dose proportional exposures with increasing dose over the 250 to 2000 mg range, low protein binding (<8% bound), no appreciable metabolism in standard in vitro assays, and renal elimination as the main excretion pathway.

Methods of Treatment

The present invention relates to a method of using imeglimin in treating metabolic disorders in patients with renal impairment or chronic kidney disease.

In certain embodiments, the patients which may be amenable to the method of this disclosure may have or are at-risk for one or more of the following diseases, disorders or conditions: type 1 diabetes, type 2 diabetes, impaired glucose tolerance (IGT), impaired fasting blood glucose (IFG), hyperglycemia, postprandial hyperglycemia, fasting hyperglycemia, latent autoimmune diabetes in adults (LADA), overweight, obesity, dyslipidemia, hyperlipidemia, hypercholesterolemia, hypertriglyceridemia, hypertension, atherosclerosis, endothelial dysfunction, osteoporosis, chronic systemic inflammation, nonalcoholic fatty liver disease (NAFLD), polycystic ovarian syndrome, metabolic syndrome, nephropathy, micro- or macroalbuminuria, proteinuria, retinopathy, cataracts, neuropathy, learning or memory impairment, neurodegenerative or cognitive disorders, cardiovascular diseases, tissue ischaemia, diabetic foot or ulcus, myocardial infarction, acute coronary syndrome, unstable angina pectoris, stable angina pectoris, peripheral arterial occlusive disease, cardiomyopathy (including e.g. uremic cardiomyopathy), heart failure, cardiac hypertrophy, heart rhythm disorders, vascular restenosis, stroke, (renal, cardiac, cerebral or hepatic) ischemia/reperfusion injuries. (renal, cardiac, cerebral or hepatic) fibrosis, (renal, cardiac, cerebral or hepatic) vascular remodeling; a diabetic disease, especially type 2 diabetes mellitus (e.g. as underlying disease).

In one aspect, the present disclosure relates to a method of treating prediabetes or type 1 or type 2 diabetes mellitus comprising administering to a subject in need thereof an effective amount of imeglimin, wherein the subject has chronic kidney disease. It is unexpected that imeglimin provides similar safety and efficacy for patients with moderate to severe chronic kidney disease compared to patients with normal renal function.

In another aspect, the presented disclosure provides a method of improving glycemic control in a subject having prediabetes or type 1 or type 2 diabetes comprising administering to the subject in need thereof an effective amount of imeglimin, wherein the subject has chronic kidney disease.

In another aspect, the presented disclosure provides a method of improving glycemic control in a subject having prediabetes or type 1 or type 2 diabetes as an adjunct to diet and exercise, comprising administering to the subject in need thereof an effective amount of imeglimin, wherein the subject has chronic kidney disease.

In some embodiments, the subject has prediabetes. In some embodiments, the subject has type 1 or type 2 diabetes mellitus. In some embodiments, the subject has type 2 diabetes mellitus.

A patient is considered to have chronic kidney disease if they have abnormalities of kidney function or structure present for more than 3 months. The definition of CKD includes all individuals with markers of kidney damage or those with an estimated Glomerular Filtration Rate (eGFR) of less than 60 ml/min/1.73 m$^2$ on at least 2 occasions 90 days apart (with or without markers of kidney damage). Markers of kidney disease may include: cystatin-C, albuminuria (albumin-to-creatinine ratio (ACR) >3 mg/mmol), haematuria (or presumed or confirmed renal origin), electrolyte abnormalities due to tubular disorders, renal histological abnormalities, structural abnormalities detected by imaging (e.g. polycystic kidneys, reflux nephropathy) or a history of kidney transplantation.

In some embodiments, CKD can be classified based on the patients' eGFR:

| Stages | Status of Kidney Function | eGFR |
| --- | --- | --- |
| Stage 1 | normal kidney function | 90 or higher |
| Stage 2 | mild loss of kidney function | 60 to 89 |
| Stage 3A | mild to moderate loss of kidney function | 45 to 59 |
| Stage 3B | moderate to severe loss of kidney function | 30 to 44 |
| Stage 4 | severe loss of kidney function | 15 to 29 |
| Stage 5 | End-stage renal disease (ESRD) | less than 15 |

In some embodiments, the subject has mild renal impairment. In some embodiments, the subject has stage 2 chronic kidney disease.

In some embodiments, the subject has mild to moderate renal impairment. In some embodiments, the subject has moderate to severe renal impairment. In some embodiments, the subject has stage 3A (or stage 3a) chronic kidney disease. In some embodiments, the subject has stage 3B (or stage 3b) chronic kidney disease. Stage 3A and stage 3B together are considered stage 3 chronic kidney disease.

In some embodiments, the subject has severe renal impairment. In some embodiments, the subject has stage 4 chronic kidney disease.

In some embodiments, the subject has stage 3B or stage 4 chronic kidney disease.

In some embodiments, the subject has an eGFR of from about 45 ml/min/1.73 m$^2$ to about 59 ml/min/1.73 m$^2$.

In some embodiments, the subject has an eGFR of from about 15 ml/min/1.73 m$^2$ to about 44 ml/min/1.73 m$^2$.

In some embodiments, the subject has an eGFR of from about 15 ml/min/1.73 m$^2$ to about 29 ml/min/1.73 m$^2$. In some embodiments, the subject has an eGFR of from about 30 ml/min/1.73 m$^2$ to about 44 ml/min/1.73 m$^2$.

In some embodiments, the subject has an eGFR of from about 30 ml/min/1.73 m$^2$ to about 59 ml/min/1.73 m$^2$.

In some embodiments, CKD can be classified based on the patients' albumin-to-creatinine ratio (ACR). Albuminuria is increased excretion of urinary albumin and a marker of kidney damage. Normal individuals excrete very small amounts of protein in the urine. Albumin-to-creatinine ratio (ACR) is a method to detect elevated protein. ACR is calculated by dividing albumin concentration in milligrams by creatinine concentration in grams. Moderately increased albuminuria, known as microalbuminuria (ACR 30-300 mg/g), refers to albumin excretion above the normal range but below the level of detection by tests for total protein. Severely increased albuminuria, known as macroalbuminuria (ACR>300), refers to a higher elevation of albumin associated with progressive decline in glomerular filtration rate.

In some embodiments, the present disclosure provides a method for treating a subject having a metabolic disorder (e.g., T2DM) and chronic kidney disease, the method comprising:
  determining the severity of the subject's chronic kidney disease;
  determining an effective dosing regimen of imeglimin for the subject based on the severity of the chronic kidney disease: and administering imeglimin to the subject according to the dosing regimen.

In some embodiments, the method comprises orally administering to a subject in need thereof an effective amount of imeglimin. In some embodiments, imeglimin can be administered to a subject via injection, such as intravenous injection.

In some embodiments, the treatment with imeglimin according to the methods described herein is well tolerated.

In some embodiments, an imeglimin-treated subject does not, or a group of imeglimin-treated subjects do not, experience an increase in frequency of lactic acidosis compared to before the subject or group of subjects initiated imeglimin treatment.

In some embodiments, an imeglimin-treated subject does not, or a group of imeglimin-treated subjects do not, experience an increase or elevation in plasma lactate compared to before the subject or group of subjects initiated imeglimin treatment.

In some embodiments, an imeglimin-treated subject does not, or a group of imeglimin-treated subjects do not, experience an increase or elevation in plasma lactate above a threshold of 3 mmol/L (27 mg/dL) compared to before the subject or group of subjects initiated imeglimin treatment.

In some embodiments, an imeglimin-treated subject is, or a group of imeglimin-treated subjects are, no more likely or less likely than placebo-treated subjects or subjects treated with a second pharmaceutical agent, including the exemplary anti-diabetic agents described herein, to experience an increase or elevation in plasma lactate compared to before the subject or group of subjects initiated imeglimin treatment.

In some embodiments, an imeglimin-treated subject has, or a group of imeglimin-treated subjects have, a similar or the same frequency of treatment-emergent adverse events as a placebo-treated subject or group of subjects.

In some embodiments, the subject or group of imeglimin-treated subjects according to the methods described herein has or have a pre-existing medical condition. In some embodiments, the pre-existing medical condition is not chronic kidney disease.

In some embodiments, an imeglimin-treated subject's or group of imeglimin-treated subjects' one or more pre-existing conditions does not or do not worsen in severity or symptomatology following treatment with imeglimin compared to that which would be expected if the subject or group of subjects took a second pharmaceutical agent, including the exemplary anti-diabetic agents described herein.

In some embodiments, an imeglimin-treated subject does not, or a group of imeglimin-treated subjects do not, experience an increase in one or more symptoms of the subject's or subjects' one or more pre-existing medical conditions compared to before the subject or subjects initiated imeglimin treatment.

In some embodiments, an imeglimin-treated subject's or group of imeglimin-treated subjects' one or more pre-existing conditions does not or do not worsen in severity or symptomatology following treatment with imeglimin. In some embodiments, the imeglimin-treated subject's or group of subjects' one or more pre-existing conditions does or do not worsen in severity or symptomatology following treatment with imeglimin compared to before the subject or subjects initiated imeglimin treatment.

In some embodiments, the pre-existing medical condition is selected from hyperkalaemia, hypertension, cardiac disorders, gastrointestinal disorders, nervous system disorders, blood and lymphatic system disorders (such as anemia), eye disorders, endocrine disorders, or combinations thereof.

In some embodiments, the pre-existing medical condition is a cardiac disorder. In some embodiments, the cardiac disorders are selected from coronary artery disease, atrial fibrillation, congestive cardiac failure, myocardial infarction, or combinations thereof.

In some embodiments, the pre-existing medical condition is a gastrointestinal disorder. In some embodiments, the gastrointestinal disorders are selected from abdominal pain, constipation, diarrhea, flatulence, gastroesophageal reflux, indigestion, nausea/vomiting, or combinations thereof.

In some embodiments, the pre-existing medical condition is a nervous system disorder. In some embodiments, the nervous system disorders are selected from diabetic neuropathy, peripheral neuropathy, or combinations thereof.

In some embodiments, the pre-existing medical condition is a blood and lymphatic system disorder. In some embodiments, the blood and lymphatic system disorders are selected from anemia, pernicious anemia, vitamin B12-dependent anemia, vitamin B12 deficiency, or combinations thereof.

In some embodiments, the pre-existing medical condition is an eye disorder. In some embodiments, the eye disorders are selected from glaucoma, cataract, or combinations thereof.

In some embodiments, the pre-existing medical condition is an endocrine or metabolism disorder. In some embodiments, the endocrine or metabolism disorders are selected from diabetes, gout, hyperuricemia, increased urate, secondary hypoparathyroidism, or combinations thereof.

In some embodiments, the amount of imeglimin administered per day is from about 500 mg to 3000 mg. In some embodiments the amount of imeglimin administered per day is from about 750 mg to about 3000 mg, from about 1000 mg to about 3000 mg, from about 1250 mg to about 3000 mg, from about 1500 mg to about 3000 mg, from about 1750 mg to about 3000 mg, from about 2000 mg to about 3000 mg, from about 2250 mg to about 3000 mg, from about 2500 mg to about 3000 mg, or from about 2750 mg to about 3000 mg.

In some embodiments, the amount of imeglimin administered per day is from about 500 mg to 2750 mg, from about 500 mg to about 2500 mg, from about 500 mg to about 2250 mg, from about 500 mg to about 2000 mg, from about 500 mg to about 1750 mg, from about 500 mg to about 1500 mg, from about 500 mg to about 1250 mg, from about 500 g to about 1000 mg, or from about 500 mg to about 750 mg.

In some embodiments, the amount of imeglimin administered per day is about 500 mg, about 550 mg, about 600 mg, about 650 mg, about 675 mg, about 700 mg, about 725 mg, about 750 mg, about 775 mg, about 800 mg, about 825 mg, about 850 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 2600 mg, about 2700 mg, about 2800 mg, about 2900 mg, about 300 mg, or in a range between any two of the preceding values.

In some embodiments, the amount of imeglimin administered per day is from about 500 mg to about 750 mg, from about 750 mg to about 1250 mg, from about 900 mg to about 1100 mg, from about 1000 mg to about 2000 mg, from about 1250 mg to about 1750 mg, or from about 1400 to about 1600 mg.

In some embodiments, the amount of imeglimin administered per day is about 1000 mg. In some embodiment, the amount of imeglimin administered per day is about 1500 mg. In some embodiments, the amount of imeglimin administered per day is about 2000 mg. In some embodiments, the amount of imeglimin administered per day is 1000 mg. In some embodiments, the amount of imeglimin is administered per day is 1500 mg. In some embodiments, the amount of imeglimin administered per day is 2000 mg.

In some embodiments, the amount of imeglimin administered to a diabetic subject with CKD per day can be substantially the same as the amount administered to a diabetic subject with normal kidney function.

In some embodiments, the amount of imeglimin administered to a diabetic subject with CKD per day is lower than the amount administered to a diabetic subject with normal kidney function.

In some embodiments, the amount of imeglimin administered to a diabetic subject with CKD (e.g., stage 3B CKD or stage 4 CKD) per day is about 20%, about 30%, about 40%, about 50%, about 60%, about 70%, about 80%, about 90%, or about 100% of the amount administered to a diabetic subject with normal kidney function, or in a range between any two preceding values, for example, from about 200/o to about 100% of the amount administered to a diabetic subject with normal kidney function.

In some embodiments, the amount of imeglimin administered to a diabetic subject with CKD (e.g., stage 3B CKD or stage 4 CKD) per day is from about 20% to about 40%, from about 20% to about 30%, from about 30% to about 50%, from about 30% to about 40%, from about 40% to about 60%, from about 40% to about 50%/c, from about 50% to about 70%, from about 50% to about 60%, or from about 60% to about 70% of the amount administered to a diabetic subject with normal kidney function.

In some embodiments, the amount of imeglimin administered to a diabetic subject with CKD (e.g., stage 3B CKD or stage 4 CKD) per day is about 750 mg, about 1000 mg, about 1500 mg, about 2000 mg, or in a range between any two preceding values.

In some embodiments, imeglimin is administered without a meal or before a meal. In some embodiments, imeglimin is administered more than two hours before a meal. In some embodiments imeglimin is administered with a meal. In some embodiments imeglimin is administered more than two hours after a meal.

In some embodiments, imeglimin is administered once per day, twice per day, or three times per day. In some embodiments, imeglimin is administered once per day. In some embodiments imeglimin is administered twice per day.

In some embodiments, imeglimin is administered to a subject about 500 mg twice a day. In some embodiments, imeglimin is administered to a subject about 750 mg twice a day. In some embodiments, imeglimin is administered to a subject about 1000 mg twice a day. In some embodiments, imeglimin is administered to a subject about 1500 mg twice a day.

In some embodiments, imeglimin is administered to a subject about 750 mg once a day. In some embodiments, imeglimin is administered to a subject about 1000 mg once a day. In some embodiments, imeglimin is administered to a subject about 1500 mg once a day.

In some embodiments, the subject is a mammal. In some embodiments, the subject is a human or an animal. In some embodiments, the subject is a human.

In some embodiments, the subject is a male. In some embodiments, the subject is a female.

In some embodiments, the subject is over the age of about 18 years. In some embodiments, the subject is under the age of about 18 years. In some embodiments, the subject is between about 6 to about 18 years, about 6 to about 12 years, or about 12 to about 18 years. In some embodiments, the subject is over the age of about 20 years. In some embodiments the subject is over the age of about 25 years. In some embodiments, the subject is over the age of about 30 years. In some embodiments, the subject is over the age of about 35 years. In some embodiments, the subject is over the age of 40 years. In some embodiments, the subject is over the age of 45 years. In some embodiments, the subject is over the age of 50 years. In some embodiments, the subject is over the age of 55 years. In some embodiments, the subject is over the age of 60 years. In some embodiments, the subject is over the age of 65 years. In some embodiments, the subject is over the age of 70 years. In some embodiments, the subject is over the age of 75 years.

In some embodiments, imeglimin is administered in the form of a free base or a pharmaceutically acceptable salt thereof. In some embodiments, imeglimin is administered in the form of a free base. In some embodiments, imeglimin is administered in the form of a pharmaceutically acceptable salt thereof. When imeglimin is in a form of a pharmaceutically acceptable salt, the salt can include salts with inorganic acid, salts with organic acid, and salts with acidic amino acid. Useful examples of the salt with inorganic acid include salts with hydrochloric acid, hydrobromic acid, nitric acid, sulfuric acid, and phosphoric acid.

Useful examples of the salt with organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, and p-toluenesulfonic acid.

In some embodiments, imeglimin is administered in the form of a hydrochloride salt. As described herein, the amount of the imeglimin administered to a subject refers to the amount of the imeglimin free base. The examples described herein may refer to "imeglimin" when imeglimin hydrochloride was used.

In some embodiments, the subject has a baseline glycosylated hemoglobin (HbA1c) percentage of from about 6.8% to about 12.0%.

In some embodiments, the subject has a baseline glycosylated hemoglobin (HbA1c) percentage of about 7.0%, about 8.0%, about 9.0%, about 10.0%, about 11.0%, or about 12.0%, or in a range between any two of the preceding values.

Efficacy of imeglimin can be assessed by measuring the change in certain parameters for the subject over a treatment period. Placebo-subtracted change or placebo-adjusted change from baseline refers to the difference between the change for subjects receiving imeglimin and the change for subjects receiving placebo. In some embodiments, the change from baseline is calculated using Lease Squares Means (LS Means).

The primary evaluation of efficacy of imeglimin is based on the level of glycosylated hemoglobin (HbA1c). The main criteria are the change in HbA1c from baseline to the end of treatment period compared to placebo.

In some embodiments, the subject experiences a placebo-subtracted decrease in glycosylated hemoglobin (HbA1c) percentage over a treatment period. In some embodiments, the placebo-subtracted decrease in HbA1c percentage over a treatment period is from about −0.5% to about −1.2%. In some embodiments, the placebo-subtracted decrease in HbA1c percentage over a treatment period is from about −0.6% to about −1.1%, from about −0.7% to about −1.0%, or from about −0.8% to about −0.9%.

In some embodiments, the placebo-subtracted decrease in HbA1c percentage over a treatment period is about −0.5%, about −0.6%, about −0.7%, about −0.8%, about −0.9%, about −1.0%, about −1.1% or about −1.2%, or in a range between any two of the preceding values. In some embodiments, the placebo-subtracted decrease in HbA1c percentage over a treatment period is about −0.8%. In some embodiments, the placebo-subtracted decrease in HbA1c percentage over a treatment period is about −1.0%.

In some embodiments, the subject experiences a placebo-subtracted decrease in fasting plasma glucose (FPG). In some embodiments, the placebo-subtracted decrease in FPG over a treatment period is from about −20 mg/dL to about −30 mg/dL. In some embodiments, the placebo-subtracted decrease in FPG over a treatment period is from about −21 mg/dL to about −28 mg/dL, from about −22 mg/dL to about −27 mg/dL, from about −23 mg/dL to about −26 mg/dL, or from about −24 mg/dL to about −25 mg/dL.

In some embodiments the placebo-subtracted decrease in FPG over a treatment period is about −20 mg/dL, about −21 mg/dL, about −22 mg/dL, about −23 mg/dL, about −24 mg/dL, about −25 mg/dL, about −26 mg/dL, about −27 mg/dL, about −28 mg/dL, about −29 mg/dL, or about −30 mg/dL, or in a range between any two of the preceding values. In some embodiments the placebo-subtracted decrease in fasting plasma glucose over a treatment period is about −25 mg/dL.

In some embodiments, the subject has daily steady-state exposures of imeglimin ($AUC_{24,ss}$) of from about 10 μg·hr/mL to about 100 μg·hr/mL. In some embodiments, the subject has daily steady-state exposures of imeglimin ($AUC_{24,ss}$) of about 10 μg·hr/mL, about 15 μg·hr/mL, about 20 μg·hr/mL, about 25 μg·hr/mL, about 30 μg·hr/mL, about 35 μg·hr/mL, about 40 μg·hr/mL, about 45 μg hr/mL, about 50 μg·hr/mL, about 55 μg·hr/mL, about 60 μg·hr/mL, about 65 μg·hr/mL, about 70 μg·hr/mL, about 75 μg hr/mL, about 80 μg·hr/mL, about 90 μg·hr/mL, about 100 μg·hr/mL, or in a range between any two of the preceding values.

In some embodiments, the subject has daily steady-state exposures of imeglimin ($AUC_{24,ss}$) of from about 10 μg·hr/mL to about 50 μg·hr/mL, from about 10 μg·hr/mL to about 40 μg·hr/mL, from about 10 μg·hr/mL to about 30 μg·hr/mL, or from about 10 μg·hr/mL to about 20 μg·hr/mL. In some embodiments, the subject has daily steady-state exposures of imeglimin ($AUC_{24,ss}$) of from about 20 μg·hr/mL to about 80 μg·hr/mL, from about 20 μg·hr/mL to about 70 μg·hr/mL, from about 20 μg·hr/mL to about 60 μg hr/mL, from about 20 μg·hr/mL to about 50 μg hr/mL, from about 20 μg·hr/mL to about 40 μg·hr/mL, or from about 20 μg·hr/mL to about 30 μg·hr/mL.

In some embodiments, the subject has received prior anti-diabetic treatment, for example, treatment for type 2 diabetes mellitus.

Prior treatment can be suitable anti-diabetic agents, including but not limited to, an acetyl-CoA carboxylase-2 (ACC-2) inhibitor, a phosphodiesterase (PDE)-10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an α-amylase inhibitor (e.g., tendamistat, trestatin and AL-3688), an α-glucoside hydrolase inhibitor (e.g., acarbose), an α-glucosidase inhibitor (e.g., adiposine, camiglibose, emiglitate, miglitol, voglibose, pradimicin-Q, and salbostatin), a PPARγ agonist (e.g., balaglitazone, ciglitazone, darglitazone, englitazone, isaglitazone, pioglitazone, rosiglitazone and troglitazone), a PPAR α/γ agonist (e.g., CLX-0940, GW-1536, GW-1929, GW-2433, KRP-297, L-796449, LR-90, MK-0767 and SB-219994), a biguanide (e.g., metformin), a glucagon-like peptide 1 (GLP-1) agonist (e.g., exendin-3 and exendin-4), a protein tyrosine phosphatase-1B (PTP-1B) inhibitor (e.g., trodusquemine, hyrtiosal extract, and compounds disclosed by Zhang, S., et al., Drug Discovery Today, 12(9/10), 373-381 (2007)), SIRT-1 inhibitor (e.g., reservatrol), a dipeptidyl peptidease IV (DPP-IV) inhibitor (e.g., sitagliptin, vildagliptin, alogliptin and saxagliptin), an insulin secreatagogue, a fatty acid oxidation inhibitor, an A2 antagonist, a c-jun amino-terminal kinase (INK) inhibitor, insulin, an insulin mimetic, a glycogen phosphorylase inhibitor, a VPAC2 receptor agonist, a glucokinase activator, and a sodium glucose transporter (SGLT2 or SGLT1/2) inhibitor.

In some embodiments, the subject has not received prior anti-diabetic treatment, for example, treatment for type 2 diabetes mellitus.

In some embodiments, imeglimin is administered with a second pharmaceutical agent. In some embodiments, imeglimin is administered concomitantly with the second pharmaceutical agent. In some embodiments, imeglimin is administered sequentially with the second pharmaceutical agent.

In some embodiments the second pharmaceutical agent is selected from the group consisting of an insulin, an alpha-glucosidase inhibitor, a biguanide, a dopamine agonist, a DPP-4 inhibitor, a glucagon-like peptide, a meglitinide, a sodium glucose transporter (SGLT2 or SGLT/2) inhibitor, a sulfonylurea, and a thiazolidinedione.

The second pharmaceutical agents can include exemplary anti-diabetic agents described herein. The second pharmaceutical agents can also include: alpha-glucosidase inhibitors, e.g., acarbose (Glucor®) and miglitol (Diastabol®): insulin sensitisers, e.g., thiazolidinediones (TZD), such as pioglitazone (Actos®) and rosiglitazone (Avandia®); agents that reduce glucogenesis, e.g., biguanides, such as metformin (Glucophage®, Stagid®); sulfonylureas (SU) such as carbutamide (Glucidoral®), glibenclamide/glyburide (Daonil®, Euglucan®), glibomuride (Glutril®), gliclazide (Diamicron®), glimepiride (Amarel®), glipizide (Glibenese®), chlorpropamide, and tolazamide: meglinides such as repaglinide (NovoNorm®): dopamine agonists, such as bromocriptine; DPP-4 inhibitors such as alogliptin, linaglip-tin, saxagliptin, sitagliptin, or vildagliptin; sodium glucose transporter (SGLT2 or SGLT 1/2) inhibitors such as dapagliflozin, canagliflozin, empagliflozin, or sotagliflozin.

In some embodiments, the second pharmaceutical agent is a DPP-4 inhibitor. In some embodiments the second pharmaceutical agent is sitagliptin.

In some embodiments, the second pharmaceutical agent is metformin.

In some embodiments, the prior anti-diabetic treatment, for example, treatment for type 2 diabetes mellitus, does not provide adequate control of or does not adequately control the subject's metabolic disorder. In some embodiments, the metabolic disorder is type 2 diabetes mellitus. In some embodiments, the prior anti-diabetic treatment does not provide adequate control of or does not adequately control the subject's glycemic parameters, non-glycemic parameters, or both. In some embodiments, the subject is not adequately controlled by the prior anti-diabetic treatment as defined by an $HbA_{1c}$ of not less than about 7.5% or by an $HbA_{1c}$ of 7.5% to 10%.

In some embodiments, the prior anti-diabetic treatment is a monotherapy. In some embodiments, the monotherapy includes a pharmaceutical agent selected from the group consisting of an insulin, an alpha-glucosidase inhibitor, a biguanide, a dopamine agonist, a DPP-4 inhibitor, a glucagon-like peptide, a meglitinide, a sodium glucose transporter (SGLT2 or SGLT1/2) inhibitor, a sulfonylurea, and a thiazolidinedione. In some embodiments, the monotherapy is a pharmaceutical agent including the exemplary anti-diabetic agents described herein.

EXAMPLES

Example 1

Comparative Effect of Imeglimin, Metformin, and Phenformin on Risks of Lactic Acidosis in Acute Renal Failure (ARF) Rat Model Metformin is associated with risk of lactic acidosis in patients with renal or/and cardiac failure. The plasma accumulation of metformin in renal insufficiency is a factor of risk for development of this lactic acidosis. Acute renal failure (ARF) can be performed in rat by gentamicin, which directly produces tubular cell necrosis and may also cause a fall in renal blood flow.

A study investigating the risk of lactic acidosis induction in rats with acute renal dysfunction after treatment with imeglimin, in comparison with biguanides metformin and phenformin was completed.

Renal failure in rats was developed following administration of gentamicin (200 mg/kg s.c.), followed by randomization: Normal (creatinine <0.6 mg/dL). Moderate (0.6 mg/dL<creatinine <2 mg/dL) and Severe renal failure (creatinine >2 mg/dL). Gentamicin was administered by subcutaneous route (administration volume: 1 ml/kg weight) once a day for 4 days. The creatinine level, correlated with the degree of the renal function failure, was tested for each rat 7 days after the first injection of gentamicin. Following administration of gentamicin, renal failure developed serum creatinine to 1 to 3 mg/dL vs. 0.5 mg/dL normal rat. The creatinine level was determined on the Monarch Chemistry Systems using the IL Test creatinine in rat plasma samples. This monochromatic analysis is based on the formation of a red colored complex between creatinine and picric acid under alkaline conditions.

Imeglimin, metformin, or phenformin dissolved in saline was administered intravenously at a constant rate of 8 ml/h/kg for 180 minutes. The doses were 100 mg/h/kg (imeglimin and metformin) and 50 mg/h/kg (phenformin) for the Normal group, and 25, 50, 75, 100 mg/h/kg (imeglimin and metformin) and 25, 50 mg/h/kg (phenformin) for the Moderate and Severe groups.

In normal rats, perfusion of imeglimin at the dose of 100 mg/h/kg significantly decreased plasma glucose from 60 minutes (6.5±0.4 vs. 7.6±0.4 mmol/L basal t p<0.001). The same effect was observed after infusion of phenformin at 50 mg/h/kg or metformin 100 mg/kg/h. But this decrease of plasma glucose was more marked in time (180 minutes) 2.9±1 mmol/L after phenformin vs. 5.4±0.4 mmol/L after imeglimin and 4±0.7 mmol/L after metformin. This hypoglycemic effect was obtained with the same plasma concentration level of imeglimin (65.16±15.8 μg/ml) and metformin (84.77+12.27 μg/ml).

In rats with mild or high ARF, the decrease in plasma glucose with imeglimin was significant and time-dependent. But differently from metformin and phenformin, severe hypoglycemia was not observed with imeglimin. Phenformin and metformin decreased plasma glucose slowly up to 120 minutes; then a sharp fall in plasma glucose appeared, 1.9±1 mmol/L for metformin and 2.4±1.1 mmol/L for phenformin.

In normal rats, metformin at 100 mg/h/kg and phenformin at 50 mg/h/kg significantly increased lactatemia. Phenformin induced higher production of lactate than metformin (9.4±2.1 vs. 4.6±0.4 mmol/L). Imeglimin did not change plasma lactate level. In ARF rats metformin and phenformin treatment significantly increased plasma lactate. This effect on plasma lactate was dose-dependent but also time-dependent. The increase in plasma lactate level induced by metformin was of greater magnitude in the rats with high ARF than those with mild ARF as defined by creatinine levels as described above. Contrary to these biguanides, imeglimin did not significantly increase plasma lactate in this ARF rat model.

In ARF rats, metformin and phenformin increased significantly plasma $H^+$ concentration. This effect appeared 2 hours after perfusion and was dose-dependent. This pH modification did not seem to correlate with degree of ARF severity for either compound. Metabolic acidosis signs with imeglimin treatment were not observed.

In ARF rats, phenformin and metformin perfusion significantly decreased plasma concentration of $[HCO_3^-]$ and this effect was dependent on severity of ARF. In groups with high creatinine level, $[HCO_3^-]$ fell significantly after metformin 100 mg/kg, 11.8±1.1 vs. 22.8±0.8 mmol/L in control p<0.001 and after phenformin at 50 mg/kg, 17.7±1.3 vs. 22.8±0.8 mmol/L in control p<0.001. Imeglimin also significantly decreased plasma $[HCO_3^-]$ vs. basal period but not vs. control group. This effect was neither dependent on degree of ARF severity nor compound concentrations.

From 50 mg/kg/h, phenformin induced 85% of mortality, which was dependent on creatinine plasma concentration. This effect appeared exclusively in the high plasma creatinine group. The main biochemical characteristics of this mortality were hypoglycemia, hyperlactatemia, drop of plasma pH (<7.2) and $[HCO_3^-]$ concentration. These biochemical alterations are the physiological hallmarks of lactic acidosis.

In the ARF rat model, plasma accumulation of metformin and imeglimin was observed. This effect appeared to be dependent on dose but also on degree of ARF severity. A significant direct relationship between plasma metformin and plasma lactate concentration was observed, r=0.758, p<0.001. Similar significant correlation appeared between plasma metformin and plasma $H^+$ concentration, r=0.611, p<0.0156. No significant correlation was observed between imeglimin plasma concentration and plasma lactate or $H^+$ levels.

Perfusion of metformin or phenformin in this acute renal failure rat model induced lactic acidosis. This lethal side effect was characterized by a dose-dependent increase of plasma lactate and $H^+$ and decrease of $[HCO_3^-]$ levels. A significant relationship between lactate level and plasma $H^+$ concentration was observed.

Example 2

A Phase 1 Clinical Study to Investigate the Pharmacokinetics of Imeglimin in Subjects with Renal Impairment Compared to Subjects with Normal Renal Function An open-label, parallel-group, multi-center, multiple oral dose study to investigate the pharmacokinetics of imeglimin in subjects with renal impairment compared to subjects with normal renal function was completed.

In this study, a total of 51 subjects received imeglimin at the daily dose of 1000 mg, administered either as 1000 mg QD (once a day) or 500 mg bid (twice a day) during 8 days. Out of 27 subjects with chronic renal impairment, 9 subjects (5 receiving QD and 4 receiving bid regimen) had mild (creatine clearance ($CL_{Crea}$) 50-80 mL/min), 12 subjects (6 receiving QD and 6 receiving bid regimen) had moderate ($CL_{Crea}$ 30 to <50 mL/min) and 6 subjects (receiving bid regimen) had severe renal impairment ($CL_{Crea}$<30 mL/min). Twenty-four control subjects with normal renal function were matched to mild and moderate (10 receiving QD and 8 receiving bid regimen) and to severe (6 receiving bid regimen) renal impaired subjects. Measurement of the urine to plasma ratio of creatinine using 24 hours urine sampling was calculated ($CL_{Crea}$).

Imeglimin was administered in the morning time during 8 consecutive days in the group of subjects receiving 1000 mg once a day and in the morning and evening time during 7 consecutive days followed by a morning administration of 500 mg in the morning time on Day 8 in the group of subjects receiving 500 mg twice a day. Morning administrations on Days 1 and 8 were performed on a fasted state, after a 10 hours overnight fasting and during 4 hours after imeglimin administration.

Inclusion Criteria: For subjects with normal renal functions: $CL_{Crea}$>80 mL/min based on calculation using 24-hrs sampling on day −2. For subjects with impaired renal function: $CL_{Crea}$ 50 to 80 mL/min for subjects with mild renal impairment, 30 to <50 mL/min for subjects with moderate renal impairment, and <30 mL/min for subjects with severe renal impairment based on calculation using 24-hrs sampling on day −2.

The mean pharmacokinetic parameters of imeglimin obtained on Day 8 of treatment are presented in Table 1 and Table 2. Pharmacokinetic parameters included apparent volume of distribution during the terminal phase following extravascular administration (Vz/F), area under the curve of the plasma concentration as a function of time ($AUC_{0-t}$), the maximum observed concentration ($C_{max}$), the time to maximum concentration ($t_{max}$), the plasma half-life ($t_{1/2}$), the total body clearance of drug from plasma following extravascular administration (CL/F), and other parameters.

Median $T_{max}$ was observed at 3.5 to 5 hours post-dose with no differences observed over renal function or time. Steady-state of imeglimin was attained by Day 6 of repeated dosing of 1000 mg QD and 500 mg bid, which is consistent with the $T_{1/2}$ (13 to 26 hours).

Figure 2:
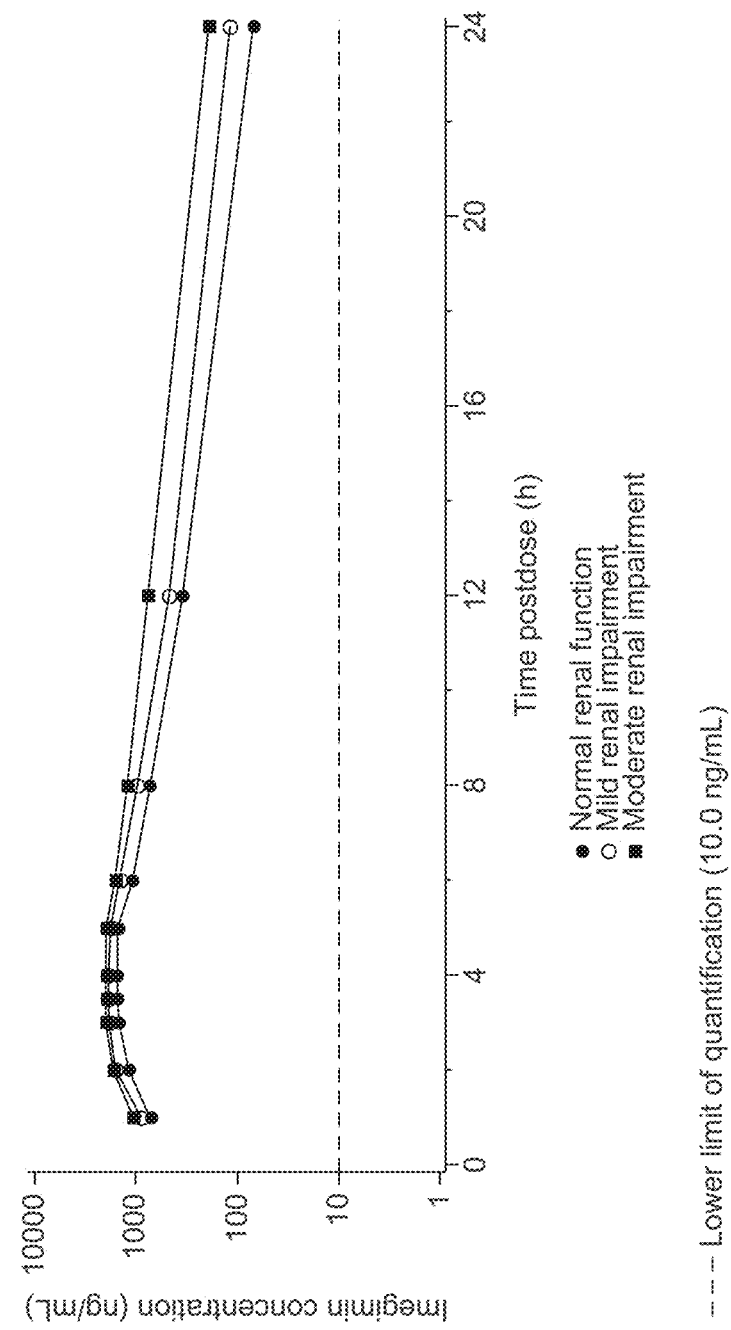
FIG. 2 depicts geometric mean plasma concentrations of imeglimin in subjects with differing degrees of renal impairment, following 1000 mg QD of imeglimin on Day 1 in a Phase 1 study (Semi-Logarithmic Scale).
Figure 3:
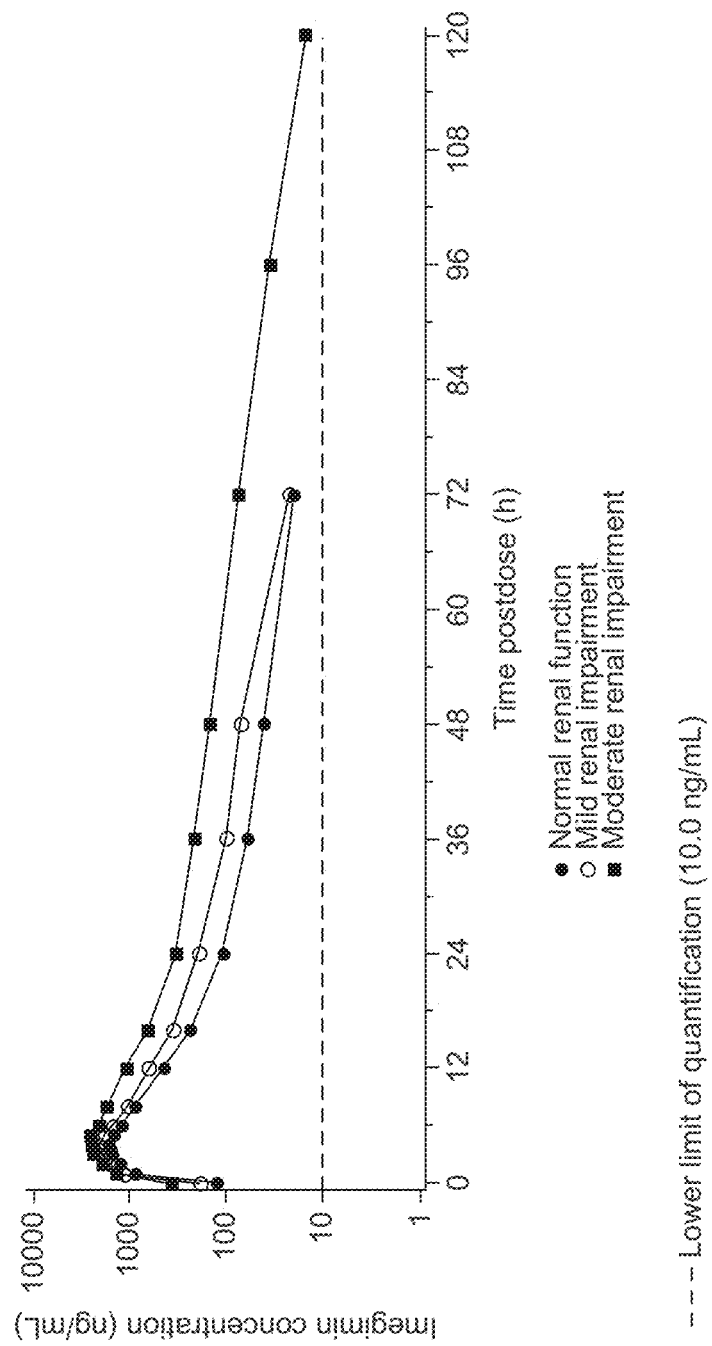
FIG. 3 depicts geometric mean plasma concentrations of imeglimin in subjects with differing degrees of renal impairment, following 1000 mg QD of imeglimin on Day 8 in a Phase 1 study (Semi-Logarithmic Scale).
Figure 4:
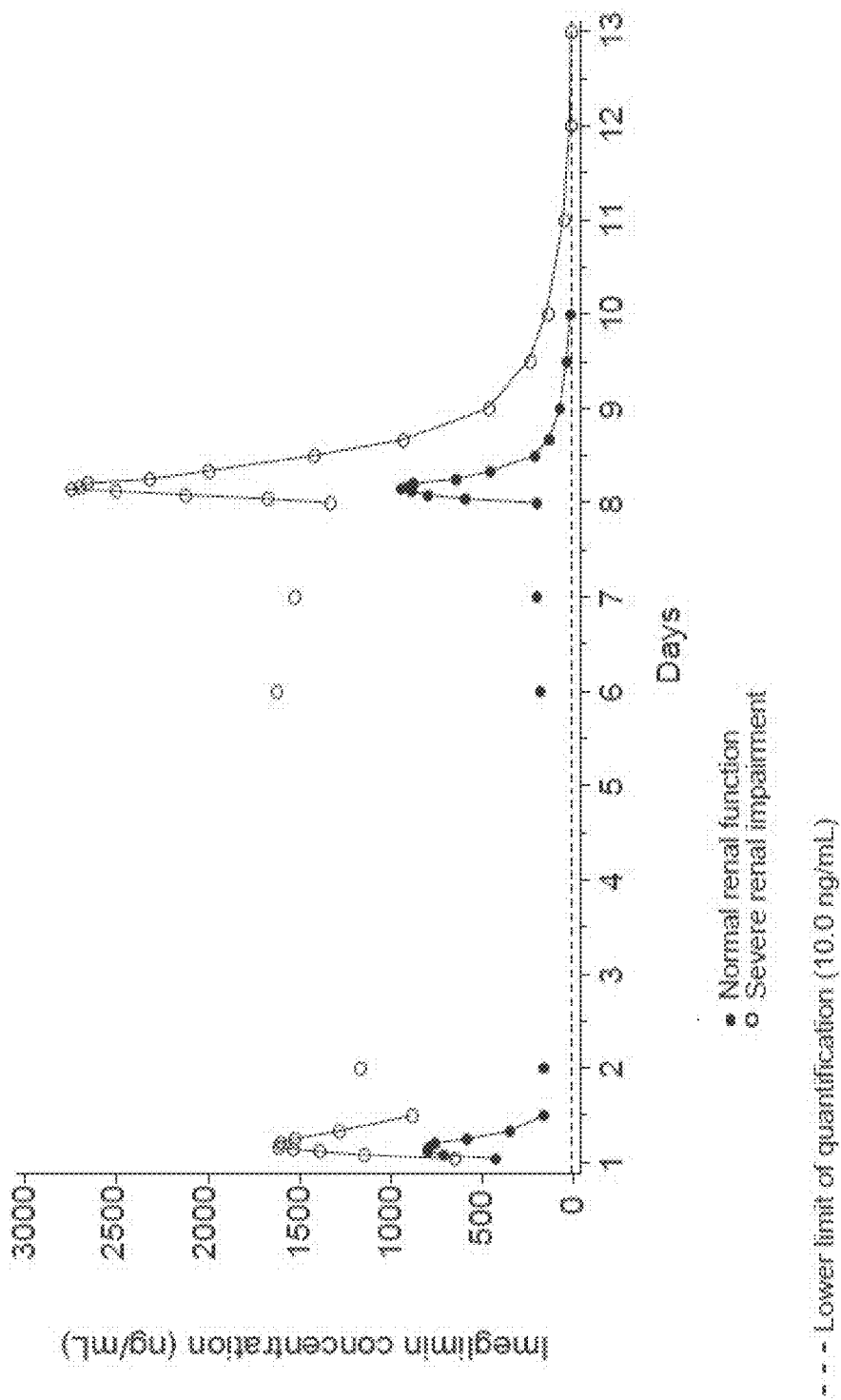
FIG. 4 depicts geometric mean plasma concentrations of imeglimin in subjects with normal renal function versus severe renal impairment, following 500) mg bid of imeglimin across all days in a Phase 1 study (Linear Scale).

Renal impairment resulted in accumulation of imeglimin by up to 3.6-fold in subjects with severe renal impairment. The difference in exposure between renal impaired subjects and normal subjects was up to 1.5-, 2.3- and 3.6-fold greater in subjects with mild, moderate and severe renal impairment, respectively on Day 8. Generally, only the increased exposure in moderate and severe groups compared to the normal renal function groups were confirmed statistically. Mean observed plasma profiles from Day 1 to Day 8 in subjects with various degrees of renal impairment, receiving 1000 mg imeglimin QD are shown in FIGS. 1-3. Mean observed plasma profiles across all days in subjects with normal renal function and severe renal impairment, receiving 500 mg imeglimin bid are shown in FIG. 4.

Total oral body clearance and renal clearance decreased with increased renal impairment by up to 72% and 74%, respectively, in subjects with severe renal impairment compared to normal subjects.

A high fraction of dose was excreted in urine for 500 mg bid regimen during the 12-hour dosing interval, with estimates of 44% to 46% in normal subjects, 43% in mild, 42% in severe and 40% in subjects with moderate renal impairment.

TABLE 1

Pharmacokinetic parameters in subjects with renal impairment following oral dose (1000 mg QD) of imeglimin on Day 8

| Parameter | Normal renal function (N = 10) | CKD stage 2 (Mild renal impairment; N = 5) | CKD Stage 3 (Moderate renal impairment; N = 6) |
|---|---|---|---|
| $AUC_{0-t}$ (ng · h/mL) | 15399 (21.2) | 20122 (15.7) | 29100 (30.4) |
| $C_{max}$ (ng/mL) | 1746 (15.9) | 2049 (26.3) | 2573 (21.2) |
| $C_{av}$ (ng/mL) | 642 (21.2) | 838 (15.7) | 1213 (30.4) |
| $C_{pre}$ (ng/mL) | 136 (71.4) | 181 (25.7) | 382 (58.1) |
| $C_{min}$ (ng/mL) | 115 (84.4) | 178 (22.6) | 335 (68.4) |
| $t_{max}$[a] (h) | 4.00 (3.00, 5.00) | 4.00 (3.00, 4.00) | 5.00 (4.00, 5.00) |
| $t_{1/2}$ (h) | 16.4 [b] (70.0) | 15.0 (74.9) | 23.4 (25.9) |
| CL/F (mL/min) | 1082 (21.2) | 828 (15.7) | 573 (30.4) |
| Vz/F (L) | 1573 [b] (56.5) | 1073 (58.8) | 1162 (38.5) |

Geometric mean (CV %) data are presented, N = Number of subjects studied,

[a]Median (min, max);

[b] N = 8.

QD = quaque die or once a day, AUC = area under the concentration-time profile, Cmax = maximum plasma concentration, t½ = elimination half-life, CL/F = apparent oral clearance, Vz/F = apparent volume of distribution.

TABLE 2

Pharmacokinetic parameters in subjects with renal impairment following oral doses (500 mg bid) of imeglimin on Day 8

| | Part 1 | | Part 2 | | |
|---|---|---|---|---|---|
| Parameter | Normal renal function (N = 8) | CKD Stage 2 (Mild renal impairment; N = 4) | CKD Stage 3 (Moderate renal impairment; N = 6) | Normal renal function (N = 6) | CKD Stage 4 (Severe renal impairment; N = 5) |
| $AUC_{0-\tau}$ (ng · h/mL) | 7389 (16.8) | 11056 (8.10) | 17168 (44.4) | 6974 (31.0) | 24833 (34.1) |
| $C_{max}$ (ng/mL) | 1028 (11.3) | 1316 (5.06) | 2001 (36.0) | 998 (29.7) | 2857 (29.1) |
| $C_{av}$ (ng/mL) | 616 (16.8) | 921 (8.10) | 1431 (44.4) | 581 (31.0) | 2069 (34.1) |
| $C_{pre}$ (ng/mL) | 254 (68.1) | 572 (9.45) | 996 (48.6) | 209 (41.8) | 1335 (37.4) |
| $C_{min}$ (ng/mL) | 202 (50.5) | 459 (15.0) | 808 (58.3) | 169 (24.6) | 1211 (44.1) |
| $t_{max}^{a}$ (h) | 3.50 (3.00, 5.02) | 4.00 (4.00, 5.00) | 3.50 (2.00, 5.00) | 3.75 (3.00, 5.00) | 3.50 (3.50, 5.00) |
| $t_{1/2}$ (h) | 13.2 (78.8) | 26.1 (20.0) | 21.9 (64.6) | 15.0 (53.2) | 17.6 (61.8) |
| CL/F (mL/min) | 1128 (16.8) | 754 (8.10) | 485 (44.4) | 1195 (31.0) | 336 (34.1) |
| Vz/F (L) | 1290 (63.0) | 1704 (23.0) | 922 (81.8) | 1548 (30.1) | 511 (102) |

Geometric mean (CV %) data are presented, N = Number of subjects studied,
[a]Median (min, max) bid = bis in die or twice a day, AUC = area under the concentration-time profile, Cmax = maximum plasma concentration, t½ = elimination half-life, CL/F = apparent oral clearance, Vz/F = apparent volume of distribution.

The urinary excretion parameters of imeglimin in subjects with differing degrees of renal impairment following QD or bid oral doses of imeglimin on day 8 are summarized in Table 3 and Table 4. Parameters measured include amount of unchanged drug excreted in urine as a function of time ($Ae_{0-t}$), renal clearance ($CL_R$), and the amount of unchanged drug excreted in urine during one dosing interval ($Ae_{0-\tau}$), and the percentage of administered dose excreted in urine during one dosing interval ($fe\tau$).

TABLE 3

Urinary excretion parameters in subjects with renal impairment, following oral doses (1000 mg QD) of imeglimin on Day 8

| Parameter | Normal renal function (N = 10) | CKD Stage 2 (Mild renal impairment) (N = 5) | CKD Stage 3 (Moderate renal impairment) (N = 6) |
|---|---|---|---|
| $Ae_{0-t}$ (mg) | 460 (22.3) | 581, 650[a] (NC) | 453 (43.4) |
| $Ae_{0-\tau}$ (mg) | 386 (27.0) | 480, 610[a] (NC) | 345 (33.2) |
| $fe_\tau$ (%) | 38.6 (27.0) | 48.0, 61.0[a] (NC) | 34.5 (33.2) |
| $CL_R$ (mL/min) | 418 (30.4) | 388, 522[a] (NC) | 197 (17.9) |

Geometric mean (CV %) data are presented, N = Number of subjects studied,
[a]N = 2; min, max presented, NC = Not calculable.

TABLE 4

Urinary excretion parameters in subjects with renal impairment, following oral doses (500 mg bid) of imeglimin on Day 8
Renal Function

| Parameter | Normal renal function (N = 8) | CKD Stage 2 (Mild renal impairment) (N = 4) | CKD Stage 3 (Moderate renal impairment) (N = 6) | Normal renal function (N = 6) | CKD Stage 4 (Severe renal impairment) (N = 5) |
|---|---|---|---|---|---|
| $Ae_{0-t}$ (mg) | 307 (37.7) | 404 (16.4) | 328 (22.6) | 298 (30.6) | 357 (25.5) |
| $Ae_{0-\tau}$ (mg) | 222 (22.6) | 215 (11.5) | 199 (29.1) | 229 (25.3) | 209 (15.6) |
| $fe_\tau$ (%) | 44.4 (22.6) | 42.9 (11.5) | 39.8 (29.1) | 45.9 (25.3) | 41.8 (15.6) |
| $CL_R$ (mL/min) | 501 (30.7) | 323 (15.0) | 193 (41.0) | 548 (11.5) | 140 (20.7) |

Geometric mean (CV %) data are presented, N = Number of subjects studied; min, max presented, NC = Not calculable.

Biochemistry and hematological parameters of subjects with normal and mild renal impairment were in most cases normal and only in single cases outside normal range. All these cases were assessed as not clinically relevant. As expected subjects with moderate and severe renal impairment showed values outside normal range for several parameters due to their underlying diseases. Urea and creatinine values were outside normal range in all cases and were assessed as clinically relevant. Hematological parameters were outside normal range in single cases and assessed as not clinically relevant, but were expected due to their underlying diseases. In single cases inorganic phosphate, ALT, GLDH, CK, triglyceride, lipase and glucose was increased in subjects with moderate and severe renal impairment and these cases were assessed as clinically relevant. No relevant deviation from normal was observed for sodium, potassium and chloride levels. There was no significant abnormality observed in the clinical laboratory parameters. Mean systolic and diastolic blood pressure values were as expected slightly higher in subjects with severe renal impairment. Vital signs did not show any clinically relevant changes following the administration of imeglimin. The mean values of PR-intervals did not show any relevant changes during the time course of the trial. QRS-, QT intervals and the corrected QTc-intervals according to Bazett and Fridericia did not reveal any relevant changes related to the administration of the study drug.

For the evaluation of safety and tolerability of multiple oral doses of 1000 mg imeglimin QD (i.e. a total dose of 8000 mg imeglimin) or 500 mg imeglimin BID (i.e. a total dose of 7500 mg imeglimin), laboratory tests (hematology, clinical chemistry, urinalysis), determination of vital signs, ECG recordings, questioning of AEs and physical examinations were performed. All safety parameters did not show any relevant changes during the course of the study. The incidence of AEs observed within the course of the study was low. Overall 31 out of 51 subjects reported 54 treatment emergent AEs. Of these, only 15 were judged as likely related to the study drug. The majority (39 AEs) were assessed as unlikely related. Based on these low incidence no clear differences between the dose regimens and between the renal impairment groups can be shown. General safety and tolerability assessment showed a good or very good tolerability of imeglimin. Overall, the safety and tolerability of a total daily dose of 1000 mg imeglimin administered either once daily or 500 mg imeglimin bid over 8 days is considered as good.

Example 3

A Dose-Ranging, Randomized, Double-Blind, Placebo-Controlled, Parallel-Group, Multi-Center Study of the Efficacy and Safety of 3 Doses of Imeglimin after 24 Weeks of Treatment in Japanese Type 2 Diabetic Subjects In this study, a total of 299 subjects with T2DM received either imeglimin at one of the 3 doses (500, 1000 and 1500 mg bid) or placebo. The primary objective of this study was to assess the dose-response of imeglimin at 3 doses (500, 1000 and 1500 mg bid) compared to placebo in male and female subjects with T2DM after 24 weeks of treatment, using glycosylated hemoglobin (HbA1c) as the primary endpoint. Inclusion Criteria: subjects have an eGFR of ≥50 mL/min/1.73 m² at screening and >=45 at pre randomization visit. A total of 299 subjects were randomized 1:1:1:1 to one of the 4 study arms, with 268 subjects completing the study.

Figure 5:
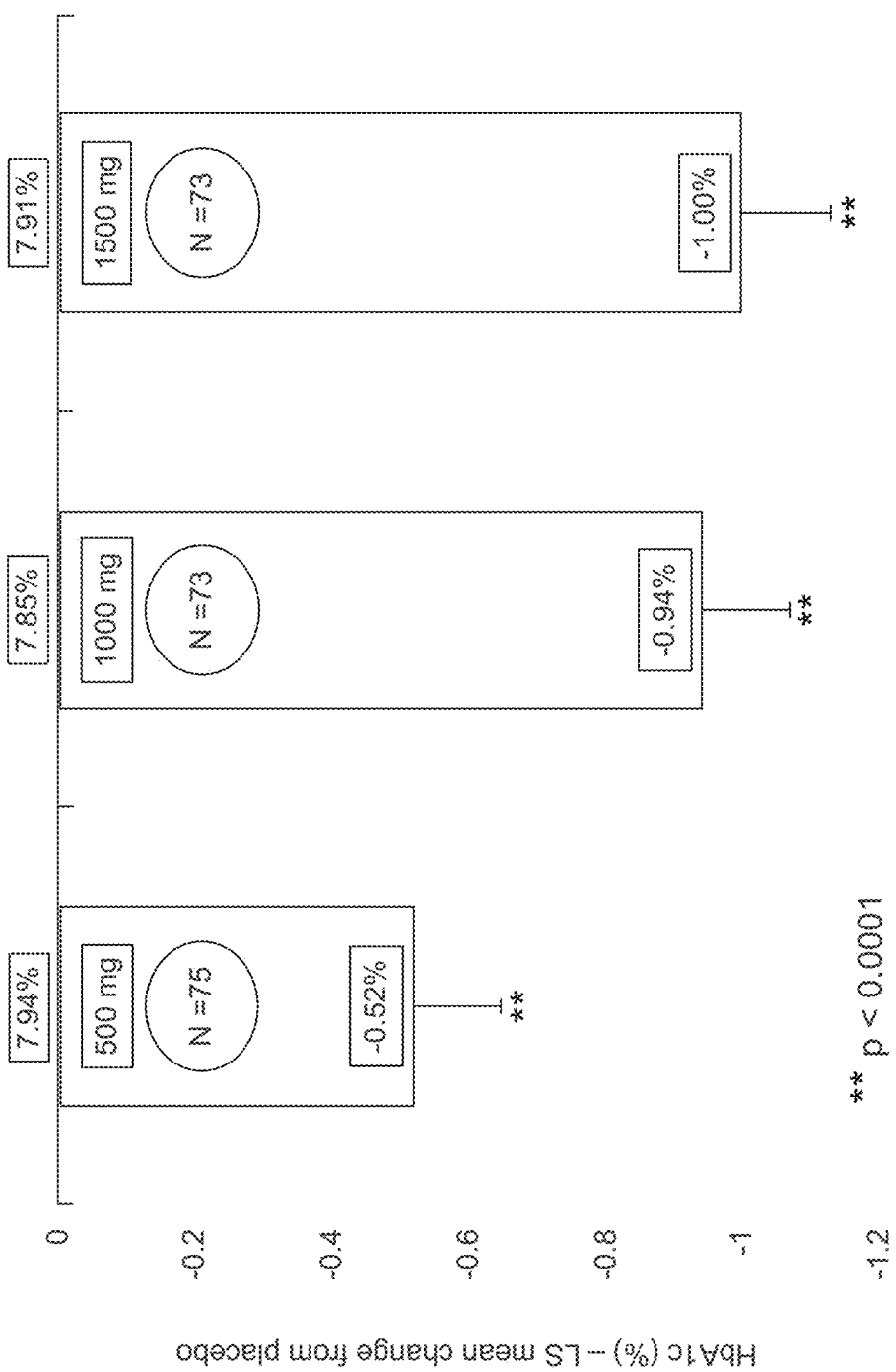
FIG. 5 depicts placebo-adjusted changes in HbA1c in three dose groups in a Phase 2b study in Japanese T2DM subjects.

The study met its primary endpoint. There was a dose-dependent decrease in placebo-adjusted change in HbA1c vs. baseline that reached statistical significance for the 3 doses (−0.52%; −0.94%, and −1.0%; p<0.0001, for 500 mg, 1000 mg and 1500 mg bid, respectively). See Table 5 and FIG. 5.

TABLE 5

| MMRM analysis of change from baseline in HbA1c (FAS) | | | | |
|---|---|---|---|---|
| FAS | Placebo N = 75 | Imeglimin 500 mg bid N = 75 | Imeglimin 1000 mg bid N = 73 | Imeglimin 1500 mg bid N = 73 |
| Baseline HbA1c (%) | 7.89 | 7.94 | 7.85 | 7.91 |
| LSM difference vs baseline (SEM) | 0.43 (0.092) | −0.09 (0.091) | −0.51 (0.093) | −0.57 (0.094) |
| LSM difference vs placebo (SEM) | | −0.52 (0.128) | −0.94 (0.129) | −1.0 (0.130) |
| P value | | <0.0001 | <0.0001 | <0.0001 |

Figure 6:
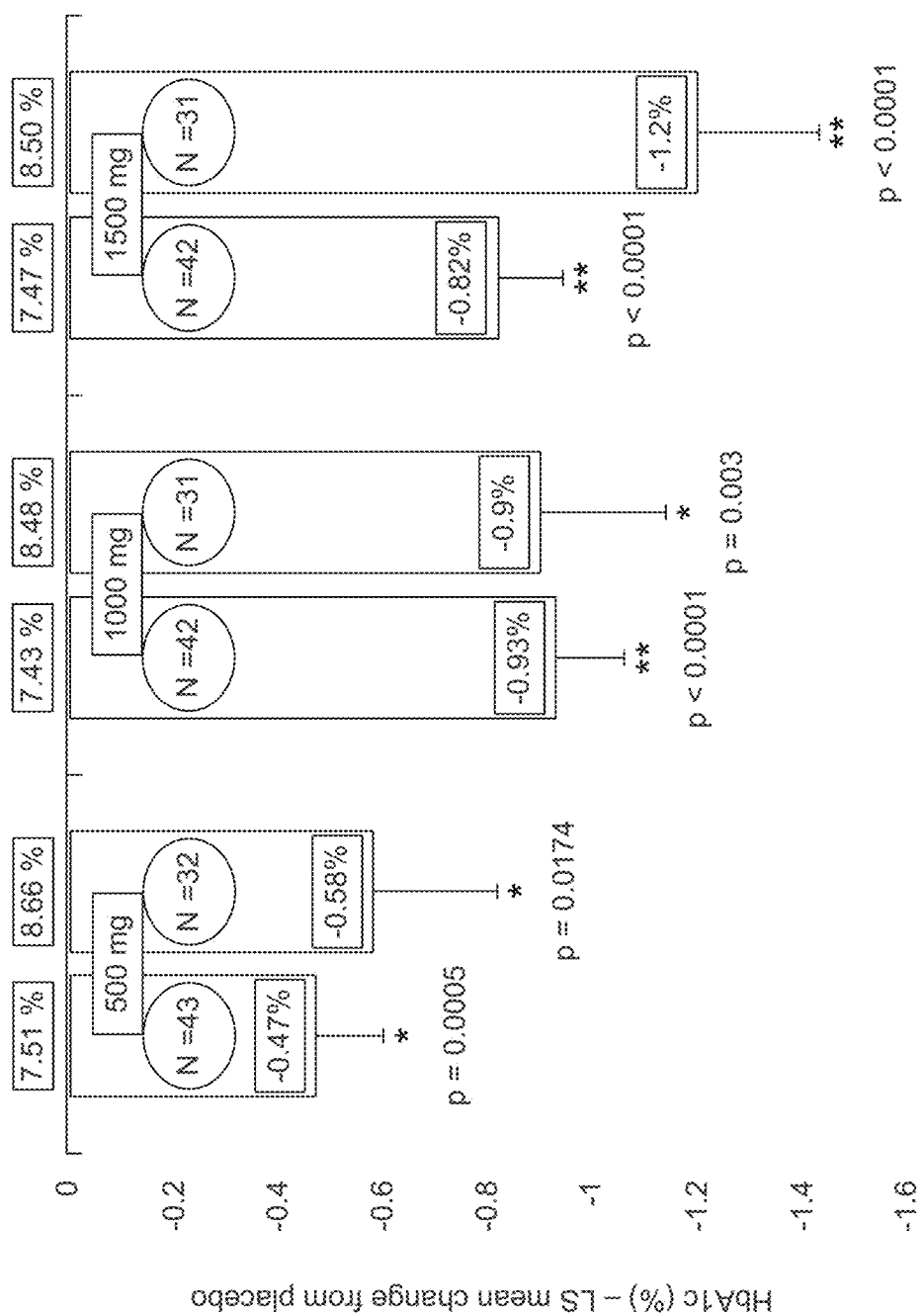
FIG. 6 depicts placebo-adjusted changes in HbA1c according to HbA1c baseline in three dose groups in a Phase 2b study in Japanese T2DM subjects.

The changes in HbA1c were analyzed depending on the baseline HbA1c<8% or ≥8%. The change in HbA1c is similar at the doses of 500 mg bid (−0.47% and −0.58% for baseline <8% and ≥8%, respectively) and 1000 mg bid (−0.93% and −0.90% for baseline <8% and ≥8%, respectively), but is larger at the dose of 1500 mg bid in the patients with higher HbA1c at baseline (−0.82% and −1.2% for baseline <8% and ≥8%, respectively). See FIG. 6.

Percentage of responders was defined as the percentage of subjects who reached a value of HbA1c≤7% at the end of the 24-week double-blind treatment period. The analysis was performed using the FAS for subjects with an HbA1c value greater than 7.0% at baseline.

Figure 7A:
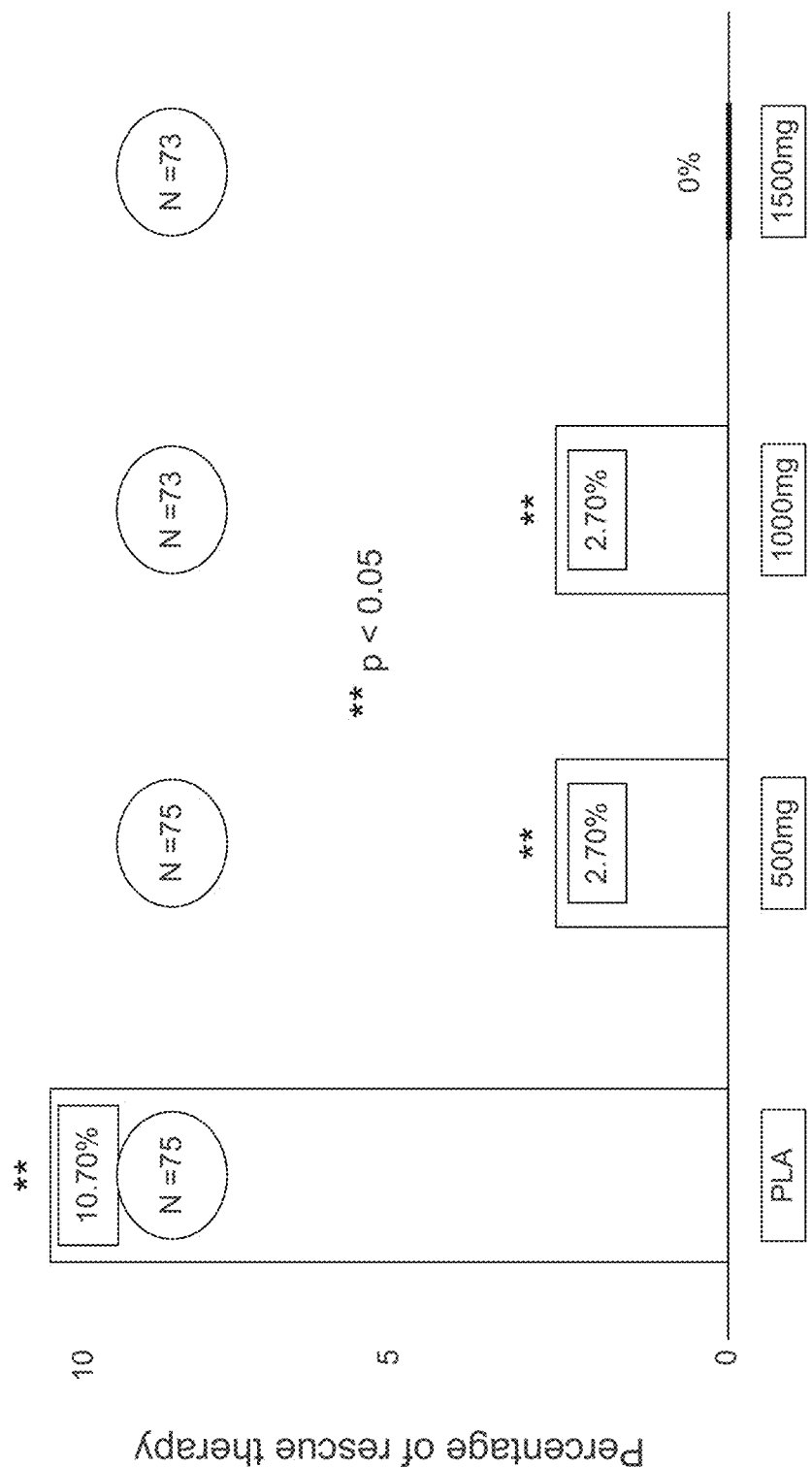
FIGS. 7A and 7B depict percentages of rescue therapy and percentages of responders in a Phase 2b study in Japanese T2DM subjects.
Figure 7B:
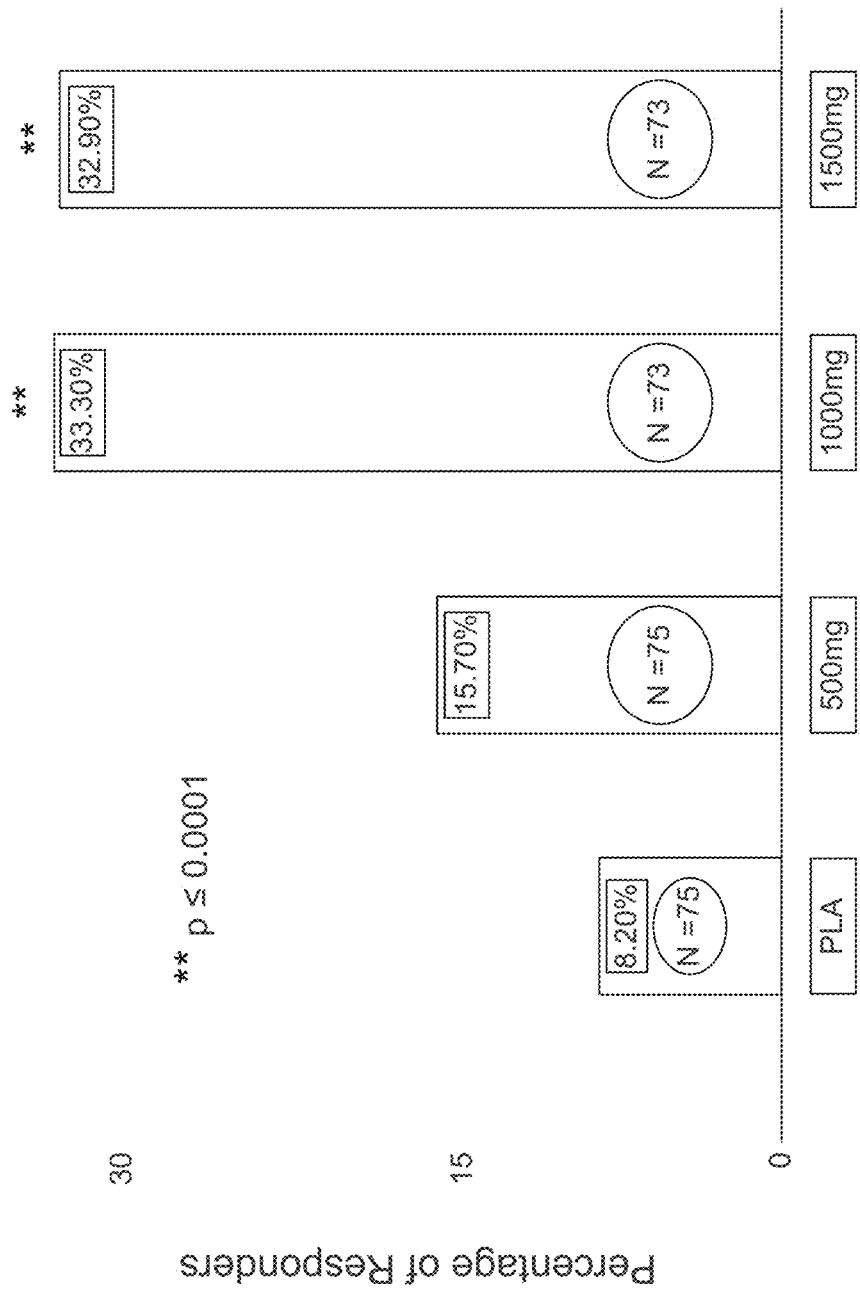

There was a statistically significant and similar increase in the responder rate in the 2 top doses of imeglimin (33.3% and 32.9% in the 1000 mg bid and 1500 mg bid imeglimin group vs. 8.2% in the placebo group). During the double blind treatment period, the percentage of subjects requiring a rescue therapy due to poor glycemic control was higher in the placebo group (10.7%) compared to other groups with no subjects requiring rescue therapy in the top dose of imeglimin 1500 mg bid. See FIGS. 7A and 7B.

Figure 8:
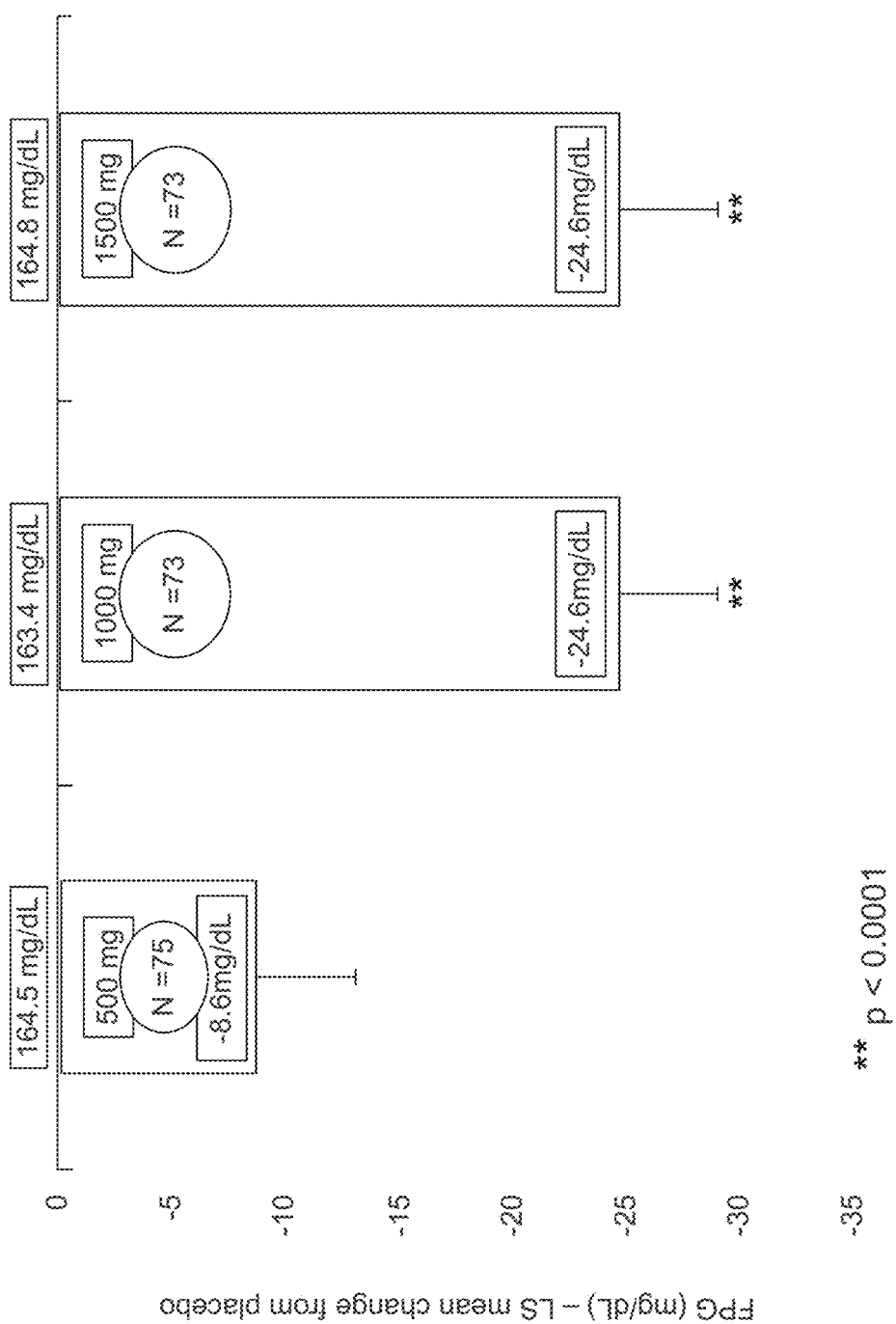
FIG. 8 depicts placebo-adjusted decrease in fasting plasma glucose (FPG) in three dose groups in a Phase 2b study in Japanese T2DM subjects.

Decrease in FPG followed the same profile with a similar effect observed at the 2 top doses of 1000 and 1500 mg bid (−24.6 mg/dL or 1.37 mmol/L p<0.001). See Table 6 and FIG. 8.

The most common adverse events are from the "Infections and Infestations" and from the "Gastrointestinal disorders" System Organ Class (SOC). Most of the TEAE were of mild intensity.

Only a few number of patients presented TEAE that were considered as related to the study drug, with a similar incidence between the placebo and the 2 first doses of imeglimin, 5.3% (imeglimin 500 mg), 5.4% (imeglimin 1000 mg) and 8% (placebo) and an increase at the top dose, 24% (imeglimin 1500 mg). This higher incidence in the latter group was partly driven by an increase in the incidence of TEAE from the gastrointestinal disorder SOC, 14.7% (placebo and imeglimin 500 mg), 18.9% (imeglimin 1000 mg) and 32% (imeglimin 1500 mg).

TEAE leading to discontinuation included both hyperglycemia requiring rescue therapy and adverse events of other SOC and were increased in the placebo (13.3%) versus the imeglimin dose groups (2.7% in 500 mg, 6.8% in the 1000) mg and 6.7% in the 1500 mg). There were no real trends among the non-hyperglycemic adverse events leading to withdrawal.

Six serious TEAEs occurred during the course of the study (5.4% in the imeglimin 1000 mg bid, 1.3% in the imeglimin 1500 mg bid and the placebo groups, none in the

TABLE 6

| | MMRM analysis of change from baseline in FPG (FAS) | | | |
|---|---|---|---|---|
| FAS | Placebo N = 75 | Imeglimin 500 mg bid N = 75 | Imeglimin 1000 mg bid N = 73 | Imeglimin 1500 mg bid N = 73 |
| Baseline FPG (mg/dL) | 160.4 | 164.5 | 163.4 | 164.8 |
| LSM difference vs baseline (SEM) | 16.6 (3.33) | 8.0 (3.29) | −8.0 (3.34) | −8.0 (3.39) |
| LSM difference vs placebo (SEM) | | −8.6 (4.40) | −24.6 (4.45) | −24.6 (4.46) |
| P value | | <0.0513 | <0.0001 | <0.0001 |

Change from baseline in Glycated Albumin (FAS) is shown in Table 7.

TABLE 7

| | MMRM analysis of change from baseline in FPG (FAS) | | | |
|---|---|---|---|---|
| FAS | Placebo N = 75 | Imeglimin 500 mg bid N = 75 | Imeglimin 1000 mg bid N = 73 | Imeglimin 1500 mg bid N = 73 |
| Baseline Glyc Alb (%) | 20.43 (4.05) | 21.23 (3.82) | 21.05 (3.89) | 20.06 (4.08) |
| LSM difference vs baseline (SEM) | 1.98 (0.429) | −0.35 (0.421) | −2.13 (0.430) | −2.25 (0.431) |
| LSM difference vs placebo (SEM) | | −2.33 (0.581) | −4.11 (0.589) | −4.23 (0.588) |
| P value | | <0.0001 | <0.0001 | <0.0001 |

The overall incidence of subjects presenting with any adverse event (AE) was similar across the groups ranging from 73% (Imeglimin 1000 mg) to 77.3% (Imeglimin 1500 mg). The incidence of subjects presenting with Treatment Emergent (TE) AE ranged from 62.2% (Imeglimin 1000 mg) to 73.3% (Imeglimn 1500 mg).

imeglimin 500 mg bid, respectively). None of them were related to the study drug. There were no real trends in the non-related serious TEAE. One serious TEAE led to death in the group of 1500 mg (metastatic pancreatic cancer discovered during the course of the study).

In conclusion, the study met its primary endpoint showing a dose-dependent decrease in placebo-adjusted HbA1c change from baseline, with the dose of 1000 mg and 1500 mg bid exhibiting a similar and maximal effect.

In a post-hoc analysis, efficacy and safety/tolerability profile was investigated in patients depending on their renal function (CKD 1=eGFR≥90 mL/min/1.73 m$^2$, CKD2=60≤eGFR <90 mL/min/1.73 m$^2$, CKD3A=45≤eGFR <60 mL/min/1.73 m$^2$). 299 patients were randomized. 74% of the patients had CKD2, 14% had CKD1, and 12% CKD3A, respectively. The primary endpoint was met with a statistically significant dose-dependent placebo subtracted decrease in HbA1c at the 3 doses with the 2 top doses of 1,000 and 1,500 mg bid reaching an HbA1c decrease of −0.94% and −100% respectively (Table 5). Imeglimin demonstrated an improvement in HbA1c lowering as compared to placebo. There were no major differences in the incidence of AE, SAE or AE leading to treatment discontinuation. No SAE or AE leading to discontinuation were observed in CKD3a subgroup.

In subjects with T2D and Stage 2 CKD reductions in HbA1c versus placebo were −0.60, −1.03, and −1.11 for 500 mg BID, 1000 mg BID, and 1500) mg BID imeglimin, respectively at 24 weeks. In addition, subjects with T2D and Stage 3a CKD reductions in HbA1c versus placebo were −0.54, −0.44, and −1.07 for 500 mg BID, 1000 mg BID, and 1500 mg BID imeglimin, respectively at 24 weeks (Table 8). Unlike the reduced HbA1c efficacy observed with SGLT2i in CKD, the preponderance of these data suggest greater HbA1c efficacy with imeglimin in subjects with CKD is independent of renal function and does not decline with CKD.

Mean Change in HbA1c (%) from baseline to Week 24 (end of treatment) for Imeglimin in Subjects broken down by eGFR category are listed in Table 8.

TABLE 8

| eGFR Sub-Category | | Placebo | Imeglimin 500 mg BID | Imeglimin 1000 mg BID | Imeglimin 1500 mg BID |
|---|---|---|---|---|---|
| Normal eGFR (eGFR > 90 mL/min/ 1.73 m$^2$) | N | 9 | 9 | 9 | 14 |
| | Week 24 LS Mean (SEM) | 0.05 (0.213) | 0.04 (0.221) | −0.8 (0.213) | −0.42 (0.175) |
| | LSM 95% CI | −0.38, 0.48 | −0.41, 0.48 | −1.23, −0.37 | −0.77, −0.06 |
| | LSM Difference vs. Placebo (SEM) | | −0.01 (0.290) | −0.85 (0.283) | −0.47 (0.260) |
| | LSM Difference vs. Placebo 95% CI | | −0.60, 0.58 | −1.43, −0.28 | −0.99, 0.06 |
| CKD Stage 2 (eGFR = 60-90 mL/min/ 1.73 m$^2$) | N | 55 | 56 | 57 | 51 |
| | Week 24 LS Mean (SEM) | 0.52 (0.112) | −0.08 (0.109) | −0.51 (0.110) | −0.58 (0.117) |
| | LSM 95% CI | 0.30, 0.74 | −0.29, 0.14 | −0.72, −0.29 | −0.81, −0.35 |
| | LSM Difference vs. Placebo (SEM) | | −0.60 (0.154) | −1.03 (0.155) | −1.11 (0.160) |
| | LSM Difference vs. Placebo 95% CI | | −0.91, −0.30 | −1.33, −0.72 | −1.42, −0.79 |
| CKD Stage 3a (eGFR < 60 mL/min/ 1.73 m$^2$) | N | 11 | 10 | 7 | 8 |
| | Week 24 LS Mean (SEM) | 0.22 (0.239) | −0.32 (0.240) | −0.22 (0.282) | −0.86 (0.265) |
| | LSM 95% CI | −0.27, 0.71 | −0.81, 0.17 | −0.80, 0.36 | −1.40, −0.31 |
| | LSM Difference vs. Placebo (SEM) | | −0.54 (0.336) | −0.44 (0.368) | −1.07 (0.353) |
| | LSM Difference vs. Placebo 95% CI | | −1.23, 0.15 | −1.19, 0.32 | −1.80, −0.35 | eGFR = estimated glomerular filtration rate; LSM = least squares mean; SEM = standard error of means; 95% CI = 95% confidence interval Fasting plasma glucose (FPG) decreased in a consistent manner in subjects with CKD Stages 2 and 3a (Table 9). Unlike reduced FPG efficacy in CKD observed with SGLT2i, the preponderance of these data suggests greater FPG efficacy with imeglimin in subjects with CKD compared to subjects with normal renal function.

Mean Change in FPG (mg/dL) from baseline to Week 24 (end of treatment) for Imeglimin in Subjects broken down by eGFR category are listed in Table 9.

TABLE 9

| eGFR Sub-Category | | Placebo | Imeglimin 500 mg BID | Imeglimin 1000 mg BID | Imeglimin 1500 mg BID |
|---|---|---|---|---|---|
| Normal eGFR (eGFR > 90) mL/min/ 1.73 m$^2$ | N | 9 | 9 | 9 | 14 |
| | Week 24 LS Mean (SEM) | 1.5 (8.80) | 15.9 (9.26) | −26.6 (8.84) | 6.6 (7.44) |
| | LSM 95% CI | −16.3, 19.2 | −2.7, 34.6 | −44.4, −8.8 | −8.4, 21.6 |
| | LSM Difference vs. Placebo (SEM) | | 14.5 (10.97) | −28.1 (10.68) | 5.1 (9.94) |
| | LSM Difference vs. Placebo 95% CI | | −7.8, 36.8 | −49.8, −6.4 | −15.1, 25.3 |

TABLE 9-continued

| eGFR Sub-Category | | Placebo | Imeglimin | | |
|---|---|---|---|---|---|
| | | | 500 mg BID | 1000 mg BID | 1500 mg BID |
| CKD Stage 2 (eGFR = 60-90 mL/min/ 1.73 m²) | N | 55 | 56 | 57 | 51 |
| | Week 24 LS Mean (SEM) | 20.0 (4.02) | 5.8 (3.93) | −6.5 (3.95) | −12.9 (4.21) |
| | LSM 95% CI | 12.1, 28.0 | −1.9, 13.6 | −14.3, 1.3 | −21.2, −4.6 |
| | LSM Difference vs. Placebo (SEM) | | −14.2 (5.30) | −26.5 (5.34) | −33.0 (5.50) |
| | LSM Difference vs. Placebo 95% CI | | −24.7, −3.8 | −37.0, −16.0 | −43.8, −22.1 |
| CKD Stage 3a (eGFR < 60 mL/min/ 1.73 m²) | N | 11 | 10 | 7 | 8 |
| | Week 24 LS Mean (SEM) | 8.4 (5.68) | 1.7 (6.03) | −2.8 (6.30) | −12.2 (6.57) |
| | LSM 95% CI | −3.1, 19.9 | −10.6, 13.9 | −15.7, 10.1 | −25.6, 1.2 |
| | LSM Difference vs. Placebo (SEM) | | −6.7 (7.77) | −11.2 (8.07) | −20.6 (7.71) |
| | LSM Difference vs. Placebo 95% CI | | −22.6, 9.1 | −27.7, 5.3 | −36.4, −4.8 | eGFR = estimated glomerular filtration rate; LSM = least squares mean; SEM = standard error of means; 95% CI 95% confidence interval Example 4

Figure 9:
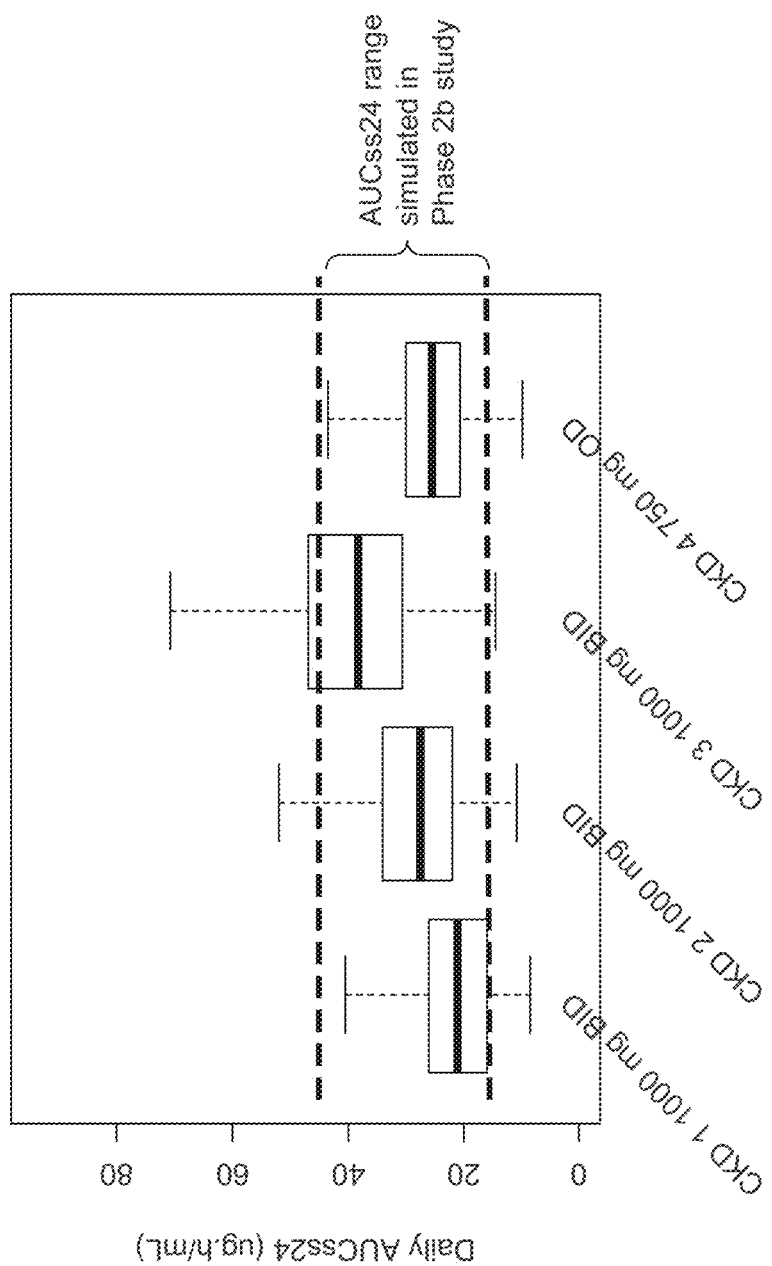
FIG. 9 depicts boxplots of $AUC_{ss24}$ simulations following imeglimin dosing regimens recommended in subjects with various stages of renal function.

A Population Pharmacokinetic (popPK) Model Study for Imeglimin in Subjects with Type 2 Diabetes Mellitus (T2DM) and in Healthy Subjects A population pharmacokinetic (popPK) model for imeglimin monotherapy after repeated oral administration in subjects with type 2 diabetes mellitus (T2DM) and in healthy subjects was developed to support the dose adjustment needed in subjects with chronic kidney disease (CKD). The popPK model was built using PK datasets from a Phase 1 study in healthy Japanese and Caucasian subjects, a Phase 1 study in renally impaired otherwise healthy Caucasian subjects, Phase 2a studies, and Phase 2b studies. The popPK model was used to simulate plasma exposure at steady-state following different dosing regimens and according to the degree of renal impairment. The simulations were performed to support the selection of dosing regimen in chronic kidney disease CKD2 (mild renal impairment), CKD3 (moderate renal impairment, including 3A and 3B) and CKD4 (severe renal impairment) subjects. Dosing regimens were defined on the basis of the efficacious doses observed in T2DM subjects. Simulations and tolerability and safety data obtained in the Phase 2b studies support the following dosage adjustment in CKD subjects: 1000 mg/1500 mg bid in subjects with normal renal function and CKD2; 1000 mg bid in CKD3 subjects; 750 mg QD in CKD4 subjects, as shown in FIG. 9.

Figure 10:
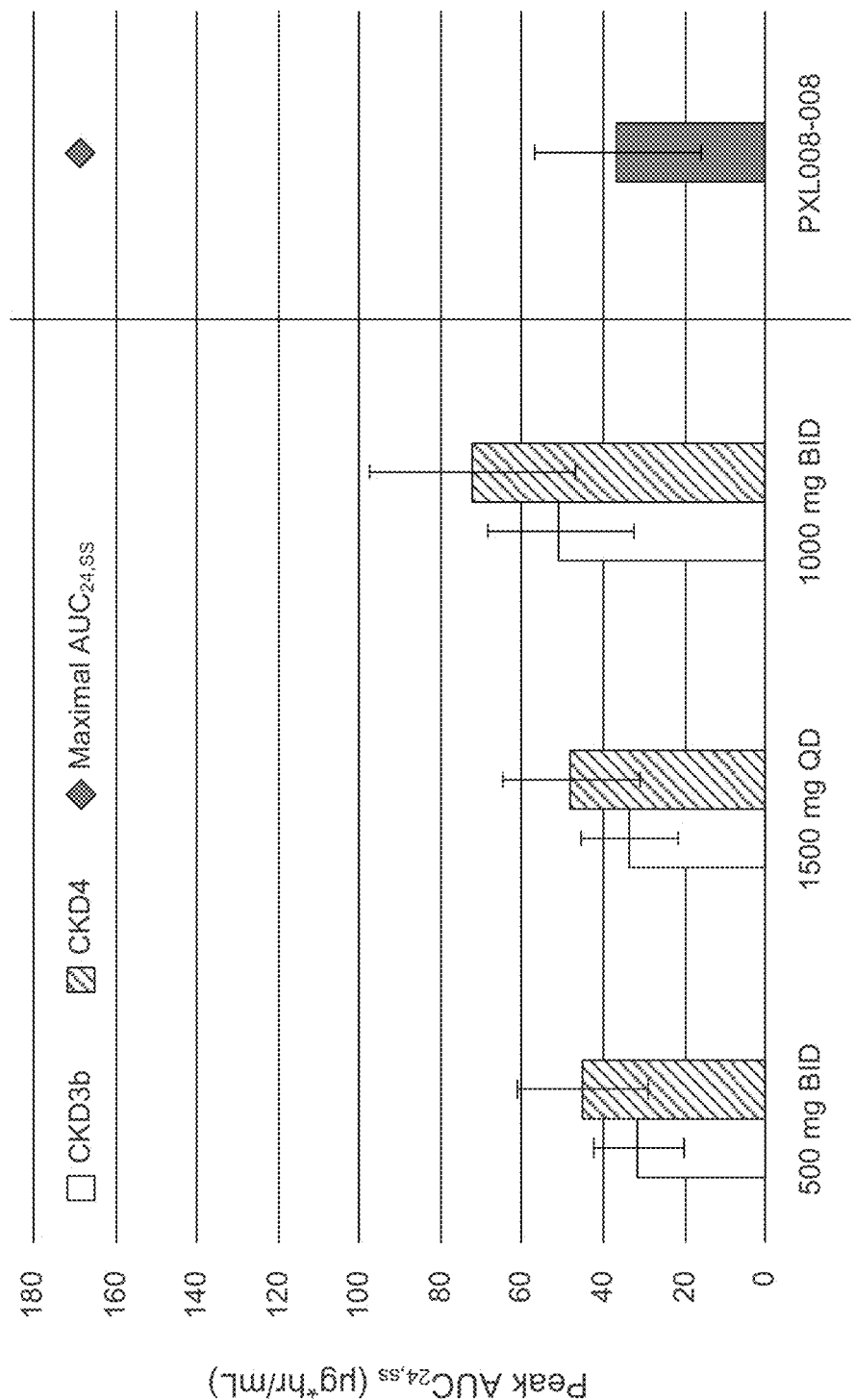
FIG. 10 depicts predicted daily steady-state exposures (mean and SD) for a Phase 1b study and actual daily steady-state exposures from a previous Phase 2b study.

In addition, predicted daily steady-state exposures ($AUC_{24,ss}$) for doses of 500 mg BID, 1500 mg QD, and 1000 mg BID in T2DM subjects with CKD stage 3B or 4 in a Phase 1b study were estimated using parameters from the population PK model: the mean $AUC_{24,ss}$ values and standard deviations are shown in FIG. 10. For reference, the mean $AUC_{24,ss}$ and standard deviation from a Phase 2b clinical study is also included in FIG. 10; the mean $AUC_{24,ss}$ in the 1500 mg BID treatment arm in that study was 36.5 µg·hr/mL (the $AUC_{24,ss}$ range was 10.1 to 169.3 µg hr/mL). At each of the three dose levels, significant overlap in exposure between T2DM subjects with CKD3B and T2DM subjects with CKD4 was predicted as evidenced by the overlap of standard deviation bars between CKD3B and CKD4 subjects at each dose level.

The dosing regimens from the simulations can be used for treating diabetic subjects with various stages of CKD.

Example 5

An Open Label, Parallel Arm Study to Assess the Safety, Tolerability, and Pharmacokinetics of Imeglimin in Subjects with Type 2 Diabetes Mellitus (T2DM) and Moderate to Severe Chronic Kidney Disease (CKD)

This Phase 1b study is to assess the safety, tolerability and pharmacokinetics (PK) of imeglimin in subjects with T2DM and CKD stage 3B or 4.

The doses included in this study are 500 mg twice daily (BID), 1500 mg once daily (QD), and 1000 mg twice daily (BID) given to subjects with type 2 diabetes and CKD stage 3B or 4 as reflected in average eGFR, calculated using the MDRD equation, of between 15 and 29 (CKD4) or 30 and 44 (CKD3B) ml/min/1.73 m², inclusive, for a treatment period of 28 days. Subjects will be randomly allocated to receive one of three treatments or placebo.

Inclusion Criteria

1) Male or female subjects who are >40 and <75 years of age.
2) Subjects diagnosed with T2DM at least 2 years prior to Screening and receiving any background regimen of approved anti-hyperglycemic medications, with the exception of metformin, at stable doses for at least 12 weeks prior to the start of screening. Subjects receiving only nonpharmacological diabetes management (diet and exercise) may also be included.
3) Subjects with type 2 diabetes and CKD stage 3B or 4 as reflected in average eGFR, based on two eGFR values taken during the Screening period at a minimum of 3 days apart, calculated using the MDRD equation of between 15 and 29 (CKD4) or 30 and 44 (CKD3B) ml/min/1.73 m², inclusive.
4) Subjects should be receiving standard of care treatment for their diabetic nephropathy with an angiotensin converting enzyme inhibitor (ACEi) and/or an angiotensin 11 receptor blocker (ARB) at a stable, therapeutically appropriate dose for at least 12 weeks prior to the start of Screening. Doses which are below the minimally acceptable doses are acceptable if stable for 12 weeks prior to Screening as per prescribing information. Subjects with intolerance to ACEi or ARB therapy documented in the medical history may be enrolled.
5) HbA1c between 6.8% and 12.0%, inclusive, at Screening.

Primary Outcome Measures

Area under the concentration-time curve from time 0 to 12 hours post-dose ($AUC_{0-12}$), maximum concentration ($C_{max}$), and time to maximum concentration ($t_{max}$) on Day 15 of each of the three dosing arms can be calculated. Changes from baseline in fasting plasma glucose (FPG), glycated albumin, and glycosylated hemoglobin (HbA1c) can also be measured.

Safety can be evaluated by assessment of clinical laboratory tests, physical examinations, vital signs measurements, and ECG readings at various time points during the study, and by the documentation of AEs.

AE verbatim text will be coded and classified by body system and preferred (coded) term using the MedDRA system organ class (SOC) and preferred term (PT).

The incidence of treatment-emergent adverse events (TEAE) will be summarized by treatment. The TEAE analyses will include the following summaries:

1) Adverse event overview for subjects with at least 1 AE in any of the following categories: AEs, SAEs, AEs with outcome of death, and AEs leading to discontinuation of investigational product;
2) All TEAEs by SOC and PT:
3) All TEAEs by preferred term and investigator's causality assessment (related vs. not related) and maximum intensity;
4) All SAEs by SOC and PT:
5) TEAEs leading to treatment discontinuation;
6) All Adverse Events of Special Interests (AESIs).

Clinical chemistry, hematology, and urinalysis values will be listed for each subject and flagged high or low relative to the normal range where appropriate. All continuous laboratory parameters will be summarized descriptively by absolute value at each visit by treatment group, together with the corresponding changes from baseline. Descriptive summary statistics will be created by treatment and visit.

Renal function is a safety parameter in this study assessed by eGFR derived from serum creatinine using the MDRD equation. Descriptive summary will be provided for eGFR, serum creatinine, urinary albumin, creatinine and the calculated urinary albumin to creatinine ratio (ACR) from a spot urine sample by treatment and visit.

Plasma lactate will be summarized descriptively by absolute value at each visit by treatment group, together with the corresponding changes from baseline.

Vital signs and physical examination will be summarized descriptively by treatment and visit. Details will be provided in the SAP.

Pharmacokinetics (PK) data can be descriptively summarized by treatment group. PK parameters will be determined using noncompartmental methods. Some PK summaries can also be displayed by baseline CKD stage groups. Steady-state can be evaluated using the trough concentration data.

The descriptive Pharmacodynamics (PD) summaries can be presented for absolute value by treatment group, together with the corresponding changes from baseline for FPG, glycated albumin and HbA1c.

Following completion of the above Phase 1b study to assess the safety, tolerability and pharmacokinetics (PK) of imeglimin in subjects with T2DM and CKD stage 3B or 4, the study data support the safety and tolerability of imeglimin in subjects having CKD stage 3B or 4.

Patients with CKD have other comorbidities that cause their CKD and contribute to the risk of cardiovascular events and death. Patients with moderate to severe CKD have an increased prevalence of these comorbidities, as evidenced by the subjects with CKD stages 3B and 4 enrolled in this study, of whom there were 100% with T2DM, 100% with hypertension, 41% with cardiac disorders. 63% with anemia. 41% with endocrine disorders, and 53% with eye disorders (Table 10). Despite the significant underlying conditions in this patient population imeglimin was well tolerated as CKD severity increased (up to stage 4) with no incidence of serious adverse events, no lactic acidosis, and no cases of confirmed plasma lactate elevations. Overall treatment-emergent adverse events (TEAE), whether or not related to study drug, were all mild or moderate and similar in frequency for imeglimin-treated subjects compared to placebo for both CKD stages 3B and 4 (Table 11). TEAEs related to study drug were almost all mild and similar in frequency between imeglimin and placebo for CKD stages 3B and 4. Gastrointestinal disorders, the most common adverse events, were similar for imeglimin-treated and placebo-treated subjects. These data suggest better gastrointestinal tolerance compared to placebo than is reported for metformin, and without an increased risk of lactic acidosis.

Figure 11:
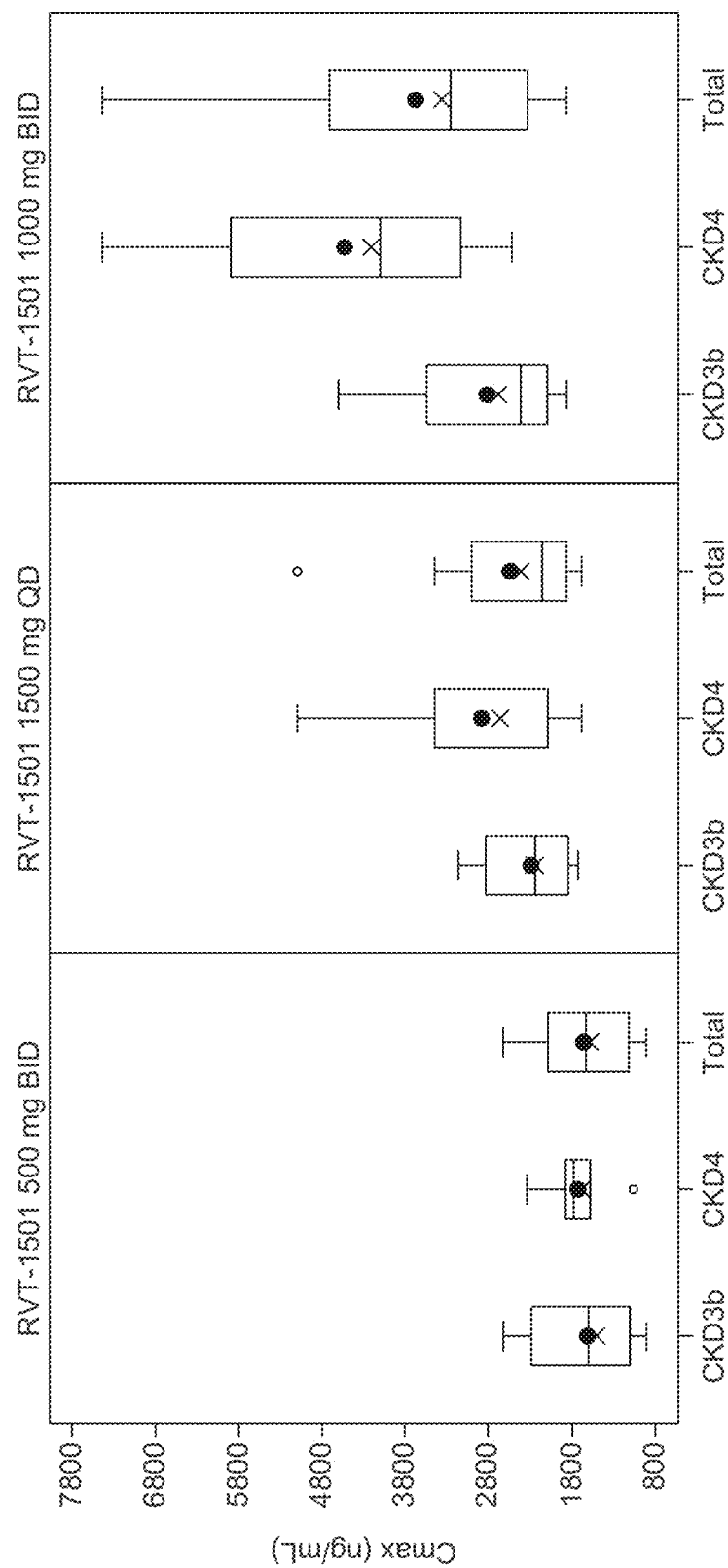
FIG. 11 depicts day 15 plasma imeglimin maximum concentrations by treatment and CKD stage. Solid circle=arithmetic mean and X=geometric mean. The box represents the first quartile (Q1), media, and third quartile (Q3). The whiskers represent the minimum observation within the lower fence and the maximum observation within the upper fence. The lower and upper fence is defined as Q1−1.5*(Q3−Q1) and Q3+1.5*(Q3−Q1), respectively.
Figure 12:
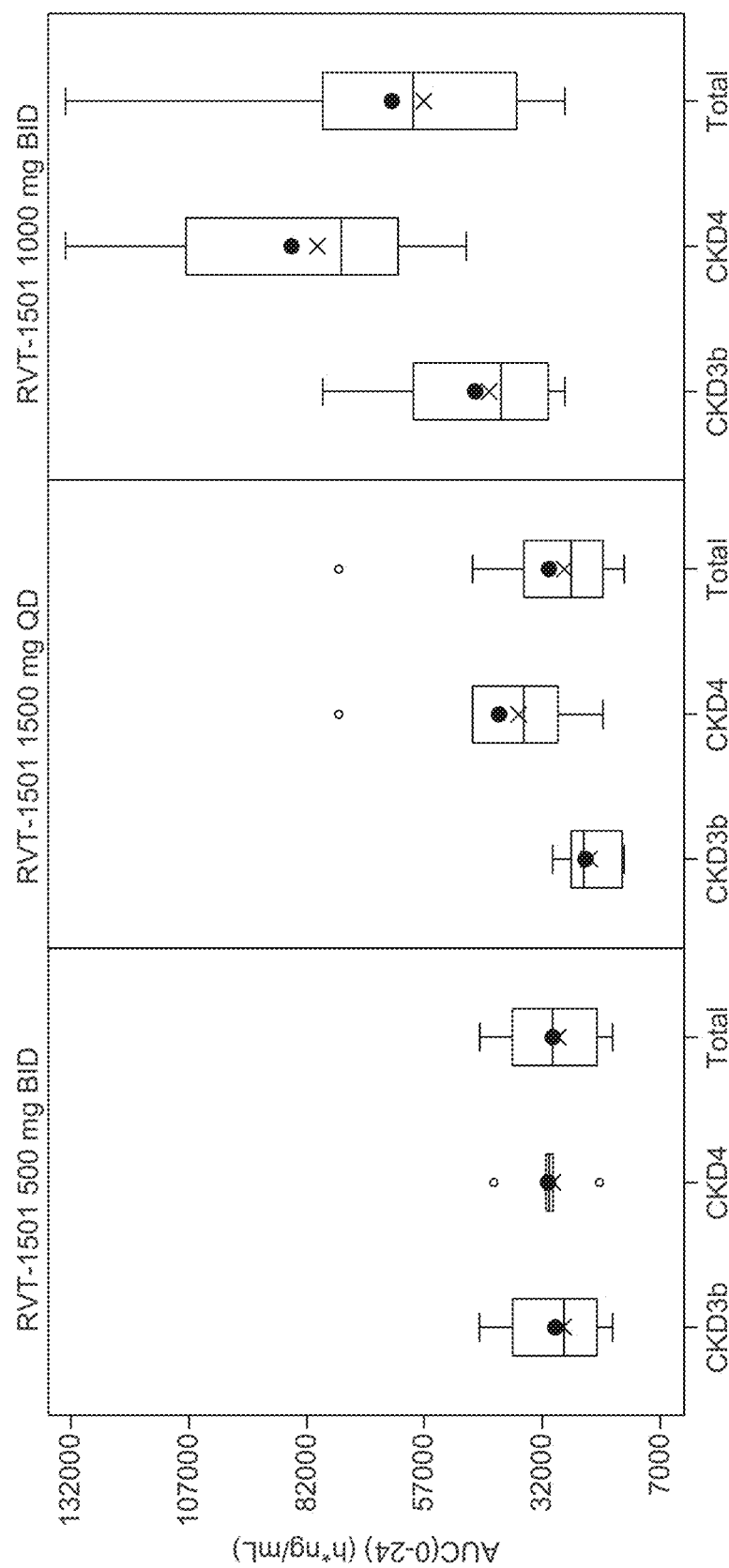
FIG. 12 depicts day 15 imeglimin area under the plasma concentration-time (AUC) profile by treatment and CKD stage. Solid circle=arithmetic mean and X=geometric mean. The box represents the first quartile (Q1), media, and third quartile (Q3). The whiskers represent the minimum observation within the lower fence and the maximum observation within the upper fence. The lower and upper fence is defined as Q1−1.5*(Q3−Q1) and Q3+1.5*(Q3−Q1), respectively.

Extensive blood sampling for pharmacokinetic analysis occurred on Day 15. After the morning dose of imeglimin on Day 15, maximum observed concentrations (Cmax) increased in a dose-dependent manner (FIG. 11). The area under the concentration-time (AUC) profiles (AUC) were similar between the 500 mg BID and 1500 mg BID treatment group but did increase in the 1000 mg BID treatment group (FIG. 12). The AUC was increased in the T2DM with CKD stage 4 compared to CKD3B in the 1500 mg QD and 1000 mg BID treatment groups (FIG. 12). This is likely due to the reduced renal filtration rate in these subjects. Despite the significant increase in systemic exposure (AUC) in the CKD stage 4 group administered with 1000 mg BID imeglimin, the incidence of adverse events was not increased compared to other treatment groups (Table 11). Surprisingly, the rate of gastrointestinal events trends at a lower rate in the 1000 mg BID treatment group compared to the 1500 mg QD treatment group despite the higher systemic exposures to imeglimin in the former (Table 11).

TABLE 10

Pre-existing Medical History by System Organ Class and Preferred Term by Treatment in Subjects with Type 2 Diabetes Mellitus (T2DM) and Moderate to Severe Chronic Kidney Disease (CKD) Enrolled in a 28 Day Study with Imeglimin

|  | Placebo (N = 11) | Imeglimin 500 mg BID (N = 13) | Imeglimin 1500 mg QD (N = 12) | Imeglimin 1000 mg BID (N = 13) | Imeglimin Total (N = 38) | Overall Total (N = 49) |
|---|---|---|---|---|---|---|
| Subjects with any medical history | 11 (100%) | 13 (100%) | 12 (100%) | 13 (100%) | 38 (100%) | 49 (100%) |
| Type 2 Diabetes Mellitus | 11 (100%) | 13 (100%) | 12 (100%) | 13 (100%) | 38 (100%) | 49 (100%) |
| Hyperkalaemia | 6 (55%) | 6 (46%) | 3 (25%) | 5 (39%) | 14 (37%) | 20 (41%) |
| Hypertension | 11 (100%) | 13 (100%) | 12 (100%) | 13 (100%) | 38 (100%) | 49 (100%) |

TABLE 10-continued

Pre-existing Medical History by System Organ Class and Preferred Term by Treatment in Subjects with Type 2 Diabetes Mellitus (T2DM) and Moderate to Severe Chronic Kidney Disease (CKD) Enrolled in a 28 Day Study with Imeglimin

|  | Placebo (N = 11) | Imeglimin 500 mg BID (N = 13) | Imeglimin 1500 mg QD (N = 12) | Imeglimin 1000 mg BID (N = 13) | Imeglimin Total (N = 38) | Overall Total (N = 49) |
|---|---|---|---|---|---|---|
| Cardiac Disorders | 2 (18%) | 6 (46%) | 8 (67%) | 4 (31%) | 18 (47%) | 20 (41%) |
| Gastrointestinal Disorders | 10 (91%) | 10 77%) | 8 (67%) | 9 (69%) | 27 (71%) | 37 (76%) |
| Nervous System Disorders | 8 (73%) | 9 (69%) | 9 (75%) | 10 (77%) | 28 (74%) | 36 (74%) |
| Musculoskeletal and Connective tissue Disorders | 9 (82%) | 10 (77%) | 7 (58%) | 8 (62%) | 25 (66%) | 34 (69%) |
| Blood and lymphatic system disorders (anemia) | 6 (55%) | 8 (62%) | 6 (50%) | 11 (85%) | 25 (66%) | 31 (63%) |
| Eye disorders | 10 (91%) | 7 (54%) | 4 (33%) | 5 (39%) | 16 (42%) | 26 (53%) |
| Endocrine Disorders | 2 (18%) | 6 (46%) | 8 (67%) | 4 (31%) | 18 (47%) | 20 (41%) |

TABLE 11

Treatment-Emergent Adverse Events in Subjects with Type 2 Diabetes Mellitus (T2DM) and Moderate to Severe Chronic Kidney Disease (CKD) Enrolled in a 28 Day Study with Imeglimin

|  | Placebo | | Imeglimin 500 mg BID | | Imeglimin 1500 mg QD | | Imeglimin 1000 mg BID | | Imeglimin Total | |
|---|---|---|---|---|---|---|---|---|---|---|
|  | CKD3b (n = 6) | CKD4 (n = 5) | CKD3b n = 8 | CKD4 (n = 5) | CKD3b (n = 17) | CKD4 (n = 5) | CKD3b (n = 6) | CKD4 (n = 7) | CKD3b (n = 21) | CKD4 (n = 17) |
| Subjects with any TEAE (n, %) | 4 (67%) | 2 (40%) | 2 (25%) | 1 (20%) | 4 (57%) | 3 (60%) | 4 (67%) | 4 (57%) | 10 (48%) | 8 (47%) |
| Subjects with any TEAE by maximum severity |  |  |  |  |  |  |  |  |  |  |
| Grade 1 - Mild | 2 (33%) | 1 (20%) | 1 (13%) | 0 | 3 (43%) | 3 (60%) | 2 (33%) | 2 (29%) | 6 (29%) | 5 (29%) |
| Grade 2 - Moderate | 2 (33%) | 1 (20%) | 1 (13%) | 1 (20%) | 1 (14%) | 0 | 2 (33%) | 2 (29%) | 4 (19%) | 3 (18%) |
| Grade 3 - Severe | 0 | 0 | 0 | 0 | 0 | 0 | 0 | 0 | 0 | 0 |
| Grade 4 - Life-threatening | 0 | 0 | 0 | 0 | 0 | 0 | 0 | 0 | 0 | 0 |
| Grade 5 - Death | 0 | 0 | 0 | 0 | 0 | 0 | 0 | 0 | 0 | 0 |
| Gastrointestinal disorders | 3 (50%) | 1 (20%) | 1 (13%) | 0 | 3 (43%) | 2 (40%) | 1 (17%) | 2 (29%) | 5 (24%) | 4 (24%) |
| Subjects with any study drug related TEAE | 2 (33%) | 1 (20%) | 0 | 0 | 1 (14%) | 2 (40%) | 2 (33%) | 1 (14%) | 3 (14%) | 3 (18%) |
| Grade 1 - Mild | 2 (33%) | 1 (20%) | 0 | 0 | 1 (14%) | 2 (40%) | 1 (17%) | 1 (14%) | 2 (10%) | 3 (18%) |
| Grade 2 - Moderate | 0 | 0 | 0 | 0 | 0 | 0 | 1 (17%) | 0 | 1 (5%) | 0 |
| Grade 3 - Severe | 0 | 0 | 0 | 0 | 0 | 0 | 0 | 0 | 0 | 0 |
| Grade 4 - Life-threatening | 0 | 0 | 0 | 0 | 0 | 0 | 0 | 0 | 0 | 0 |
| Grade 5 - Death | 0 | 0 | 0 | 0 | 0 | 0 | 0 | 0 | 0 | 0 |

Example 6

A 24-Week, Phase IIb, Dose-Ranging, Randomized, Double-blind. Placebo-controlled, Parallel-group Safety and Efficacy Study in Subjects with T2DM The five parallel groups included 4 groups of imeglimin doses (500, 1000, 1500, or 2000 mg twice daily) and 1 placebo group. The primary endpoint was to assess the dose-response in T2D subjects, using change in HbA1c from baseline to week 24 as the primary evaluation criterion. Subjects could be either treatment naïve or treated with any oral antidiabetic monotherapy and were to have an eGFR of ≥50 mL/min/1.73 m². A total of 382 subjects were randomized 1:1:1:1:1 to one of the 5 study arms, with 315 subjects completing the study. In a post-hoc analysis of subjects with T2D and stage 2 and 3a CKD [eGFR of <90 mL/min/1.73 m² (n=211)], imeglimin demonstrated an improvement in HbA1c lowering as compared to placebo.

Mean Change in HbA1c (%) from baseline to Week 24 (end of treatment) for Imeglimin in Subjects with T2D and Stage 2 and 3a CKD are listed in Table 12 below

TABLE 12

| Treatment | Mean (SD) HbA1c Change from Baseline |
|---|---|
| Placebo (n = 41) | 0.161 (0.878) |
| 500 mg BID (n = 44) | 0.007 (1.06) |
| 1000 mg BID (n = 43) | −0.072 (0.996) |
| 1500 mg BID (n = 41) | −0.502 (0.855) |
| 2000 mg BID (n = 42) | −0.193 (1.06) |

Example 7

A 24-Week Phase III, Randomized, Double-Blind, Placebo-Controlled, Monotherapy Study to Assess the Efficacy, Safety and Tolerability of Imeglimin Administered Orally in Japanese Patients with Type 2 Diabetes (T2DM)

A total of 213 subjects were randomized in a 1:1 ratio to receive either imeglimin (1000 mg BID) or placebo BID for 24 weeks, with 194 subjects completing the study without Investigational Medicinal Product (IMP) discontinuation. The primary objective of this study was to determine the change in HbA1c from baseline after 24 weeks of imeglimin treatment compared to placebo. Secondary endpoints of the trial included fasting plasma glucose along with other standard glycemic and non-glycemic parameters. Subjects were to have an eGFR of ≥50 mL/min/1.73 m² at Screening and ≥45 mL/min/1.73 m² at Pre-randomization. In a pre-specified analysis of subjects with T2D and stage 2 and 3a CKD [eGFR of <90 mL/min/1.73 m² (n=178)], imeglimin demonstrated an improvement in A1C lowering as compared to placebo.

In this study, HbA1c reduction was evaluated at Week 24. In subjects with normal eGFR (>90 mL/min/1.73 m²) treated with imeglimin 1000 mg BID, the placebo corrected HbA1c reduction was −0.59%. The placebo corrected HbA1c reduction was larger in subjects with CKD: −0.96% and −0.70% for stage 2 CKD and stage 3a CKD, respectively. Similar to the results from Example 3, the preponderance of these data suggest greater HbA1c efficacy with imeglimin in subjects with CKD is independent of renal function and does not decline with CKD.

Mean Change in HbA1c (%) from baseline to Week 24 (end of treatment) for Imeglimin in Subjects broken down by eGFR category are listed in Table 13 below.

TABLE 13

| eGFR Sub-Category | | Placebo | Imeglimin 1000 mg BID |
|---|---|---|---|
| Normal eGFR (eGFR > 90 mL/min/1.73 m²) | N | 5 | 11 |
| | Week 24 LS Mean (SE) | 0.26 (0.27) | −0.33 (0.20) |
| | LSM 95% CI | −0.32, 0.84 | −0.77, 0.10 |
| | LSM Difference vs. Placebo (SE) | | −0.59 (0.32) |
| | LSM Difference vs. Placebo 95% CI | | −1.30, 0.11 |
| CKD Stage 2 (eGFR = 60-90 mL/min/1.73 m²) | N | 75 | 66 |
| | Week 24 LS Mean (SE) | 0.14 (0.08) | −0.82 (0.08) |
| | LSM 95% CI | −0.02, 0.31 | −0.99, −0.65 |
| | LSM Difference vs. Placebo | | −0.96 (0.11) |
| | LSM Difference vs. Placebo 95% CI | | −1.17, −0.75 |
| CKD Stage 3a (eGFR < 60 mL/min/1.73 m²) | N | 16 | 21 |
| | Week 24 LS Mean (SE) | 0.04 (0.14) | −0.66 (0.13) |
| | LSM 95% CI | −0.24, 0.32 | −0.93, −0.40 |
| | LSM Difference vs. Placebo | | −0.70 (0.19) |
| | LSM Difference vs. Placebo 95% CI | | −1.08, −0.32 | eGFR = estimated glomerular filtration rate; LSM = least squares mean; SE = standard error; 95% CI = 95% confidence interval

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents, patent applications, and other publications cited herein are fully incorporated by reference herein in their entirety.

What is claimed is:

1. A method of treating type 2 diabetes mellitus comprising administering to a subject in need thereof an effective amount of imeglimin to produce daily steady-state exposures of imeglimin ($AUC_{24,ss}$) from about 20 µg·hr/mL to about 60 µg·hr/mL, wherein the subject has stage 3B or stage 4 chronic kidney disease, and wherein the amount of imeglimin is about 1000 mg to about 3000 mg per day.

2. The method of claim 1, wherein the subject has an estimated glomerular filtration rate (eGFR) of between about 30 ml/min/1.73 m² and about 44 ml/min/1.73 m².

3. The method of claim 1, wherein the subject has an estimated glomerular filtration rate (eGFR) of between about 15 ml/min/1.73 m² and about 29 ml/min/1.73 m².

4. The method of claim 1, wherein the subject has one or more pre-existing medical conditions.

5. The method of claim 4, wherein the one or more pre-existing medical condition is not chronic kidney disease and is selected from hyperkalaemia, hypertension, cardiac disorders, gastrointestinal disorders, nervous system disorders, blood and lymphatic system disorders (such as anemia), eye disorders, endocrine disorders, or combinations thereof.

6. The method of claim 4, wherein the imeglimin-treated subject's one or more pre-existing medical conditions do not worsen in severity or symptomatology following treatment with imeglimin.

7. The method of claim 4, wherein the one or more pre-existing medical condition is a gastrointestinal disorder.

8. The method of claim 1, wherein the imeglimin-treated subject does not experience an increase in frequency of lactic acidosis compared to before the subject initiated imeglimin treatment.

9. The method of claim 1, wherein the amount of imeglimin is about 1500 mg to about 3000 mg per day.

10. The method of claim 9, wherein imeglimin is administered about 500 mg twice a day, about 1000 mg twice a day, or about 1500 mg once a day.

11. The method of claim 1, wherein imeglimin is administered in the form of a hydrochloride salt.

12. The method of claim 1, wherein the subject experiences a placebo-subtracted decrease in glycosylated hemoglobin (HbA1c) percentage of between about 0.5% and about 1.2% over a treatment period.

13. The method of claim 1, further comprising administering to the subject a second pharmaceutical agent.

14. A method of improving glycemic control in a subject having type 2 diabetes comprising administering to the subject in need thereof an effective amount of imeglimin to produce daily steady-state exposures of imeglimin ($AUC_{24,ss}$) from about 20 µg·hr/mL to about 60 µg·hr/mL, wherein the subject has stage 3B or stage 4 chronic kidney disease, and wherein the amount of imeglimin is about 1000 mg to about 3000 mg per day.

15. The method of claim 14, wherein the subject has an estimated glomerular filtration rate (eGFR) of between about 30 ml/min/1.73 m² and about 44 ml/min/1.73 m².

16. The method of claim 14, wherein the subject has an estimated glomerular filtration rate (eGFR) of between about 15 ml/min/1.73 m$^2$ and about 29 ml/min/1.73 m$^2$.

17. The method of claim 14, wherein the subject experiences a placebo-subtracted decrease in glycosylated hemoglobin (HbA1c) percentage of between about 0.5% and about 1.2% over a treatment period.

18. The method of claim 9, wherein the treatment period is from about 4 weeks to about 52 weeks.

19. The method of claim 14, wherein said administering of imeglimin is used as an adjunct to diet and exercise.

20. The method of claim 1, wherein the daily steady-state exposure of imeglimin (AUC$_{24,ss}$) is about 30 µg·hr/mL.

* * * * *